US012304889B2

(12) United States Patent
Tatamidani et al.

(10) Patent No.: US 12,304,889 B2
(45) Date of Patent: May 20, 2025

(54) METHOD FOR PRODUCING CIS-(-)-FLOCINO PIPERIDOL

(71) Applicant: SUMITOMO PHARMA CO., LTD., Osaka (JP)

(72) Inventors: Hiroto Tatamidani, Osaka (JP); Shinjiro Tsuyumine, Osaka (JP); Yoko Takahashi, Osaka (JP)

(73) Assignee: Sumitomo Pharma Co., LTD., Osaka (JP)

( * ) Notice: Subject to any disclaimer, the term of this patent is extended or adjusted under 35 U.S.C. 154(b) by 0 days.

(21) Appl. No.: 17/603,536

(22) PCT Filed: Apr. 17, 2020

(86) PCT No.: PCT/JP2020/016885
§ 371 (c)(1),
(2) Date: Oct. 13, 2021

(87) PCT Pub. No.: WO2020/213714
PCT Pub. Date: Oct. 22, 2020

(65) Prior Publication Data

US 2022/0220072 A1 Jul. 14, 2022

(30) Foreign Application Priority Data

Apr. 18, 2019 (JP) ................................ 2019-079299

(51) Int. Cl.
*C07D 211/42* (2006.01)
*C07B 57/00* (2006.01)

(52) U.S. Cl.
CPC ............ *C07D 211/42* (2013.01); *C07B 57/00* (2013.01)

(58) Field of Classification Search
CPC .................................................... C07D 221/42
See application file for complete search history.

(56) References Cited

U.S. PATENT DOCUMENTS 4,900,727 A * 2/1990 Kattige ................... A61P 25/04 540/596
5,849,733 A * 12/1998 Kim ..................... C07D 405/04 540/596
5,908,934 A * 6/1999 Kim ..................... C07D 405/04 546/186

FOREIGN PATENT DOCUMENTS

WO 98/13344 A1 4/1998

OTHER PUBLICATIONS

Chikashita "Stereoselective syn-reduction of (R)-4-acyl-2,2-dimethyl-1,3-dioxolanes with metal hydride reagents." Bulletin of the Chemical Society of Japan, 1989, 62(6), 2121-3.*
Hubbard "Lithium Tri-sec-butylborohydride1" Encyclopedia of Reagents for Organic Synthesis 2012, pp. 1-6.*
Kozma "CRC Handbook of Optical Resolutions Via Diastereomeric Salt Formation" 2002 CRC Press: Washington, DC, Chapters 6.*
Caron, "Large-Scale Oxidations in the Pharmaceutical Industry" Chemical Reviews 2006, 106(7), 2943-2989.*
Arai "Carbonyl Hydroboration" Chapter 7 in Modern Reduction Methods. Edited by Pher G. Andersson and Ian J. Munslow. 2008 WILEY-VCH Verlag GmbH & Co. KGaA, Weinheim.*
Kim et al., "Thio- and Oxoflavopiridols, Cyclin-Dependent Kinase 1-Selective Inhibitors: Synthesis and Biological Effects," *J. Med. Chem.* 43:4126-4134, 2000.
Naik et al., "An Antiinflammatory Cum Immunomodulatory Piperidinylbenzopyranone From Dysoxylum Binectariferum: Isolation, Structure and Total Synthesis," *Tetrahedron* 44(7):2081-2086, 1988.
The Chemical Society of Japan, "The fifth series of experimental chemistry 14, Synthesis of Organic Compounds II—alcohol and amine", (with English translation), Maruzen Inc., 2005 (26 pages).
The Chemical Society of Japan, "The fourth series of experimental chemistry 26, Organic Synthesis VIII—asymmetric synthesis, reduction, sugar, and labeled compound", (with English translation), Maruzen Inc., 1992 (4 pages).
The Chemical Society of Japan, "The fifth series of experimental chemistry 17, Synthesis of Organic Compounds V—oxidation reaction," (with English translation), Maruzen Inc., 2004 (92 pages).

* cited by examiner

*Primary Examiner* — David K O'Dell
(74) *Attorney, Agent, or Firm* — Seed IP Law Group LLP

(57) ABSTRACT

The present invention provides a method in which when using (+)-dibenzoyl-D-tartaric acid to optically divide (±)-1-methyl-4-(2,4,6-trimethoxyphenyl)-3-piperidinone, an ether-based solvent is added and an extremely high yield of (R)-1-methyl-4-(2,4,6-trimethoxyphenyl)-3-piperidinone (+)-dibenzoyl-D-tartrate is thereby obtained, a slurry thereof is treated with a base, a "three-dimensionally bulky reducing agent" is subsequently used, and cis-(−)-flocinopiperidol is thereby produced with surprisingly high selectivity.

14 Claims, No Drawings

METHOD FOR PRODUCING CIS-(-)-FLOCINO PIPERIDOL

TECHNICAL FIELD

The present invention relates to a manufacturing method of various intermediates of alvocidib, which is useful as a pharmaceutical product.

BACKGROUND ART

Alvocidib (flavopiridol, chemical name: 2-(2-chlorophenyl)-5,7-dihydroxy-8-[(3S,4R)-3-hydroxy-1-methylpiperidin-4-yl]-4H-1-benzopyran-4-one) is a synthetic flavone having the following structure:

[Chemical Formula 1]

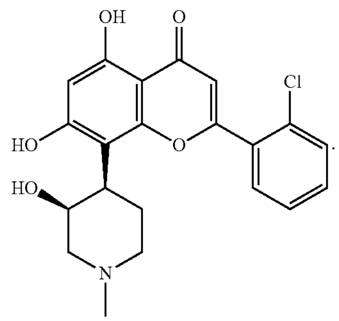

Alvocidib is a potent and selective inhibitor of cyclin-dependent kinase (CDK) and an attractive therapeutic agent for cancer. Currently, clinical development for use in hematological cancer is ongoing.

For example, the methods described in Patent Literature and Non Patent Literature 1 are known as a method of manufacturing cis-(−)-flocinopiperidol associated with an intermediate of alvocidib. Further, Non Patent Literature 2, Patent Literature 2, and Patent Literature 3 are known as a method of manufacturing 1-methyl-4-(2,4,6-trimethoxyphenyl)piperidin-3-one, which is an intermediate for the manufacture of cis-(−)-flocinopiperidol.

Patent Literature 1 and Non Patent Literature 1 describe a method of obtaining cis-(−)-flocinopiperidol from (±)-1-methyl-4-(2,4,6-trimethoxyphenyl)piperidin-3-one.

Patent Literature 2 and Non Patent Literature 2 describe a method of obtaining cis-(−)-flocinopiperidol from (±)-1-methyl-4-(2,4,6-trimethoxyphenyl)piperidin-3-ol.

Patent Literature 3 describes a method of obtaining cis-1-methyl-4-(2,4,6-trimethoxyphenyl)piperidin-3-one from (±)-1-methyl-4-(2,4,6-trimethoxyphenyl)piperidin-3-ol.

CITATION LIST

Patent Literature

[PTL 1] International Publication No. WO 98/13344
[PTL 2] U.S. Pat. No. 4,900,727
[PTL 3] U.S. Pat. No. 5,849,733

Non Patent Literature

[NPL 1] K. S. Kim, et al., J. Med. Chem. 43, 4126 (2000)
[NPL 2] R. Naik., et al., Tetrahedron 44, 2081 (1988)

SUMMARY OF INVENTION

Solution to Problem

The present invention relates to a method of manufacturing cis-(−)-flocinopiperidol, which is suitable for industrial production. Specifically, the present invention provides a method of manufacturing highly pure cis-(−)-flocinopiperidol safely and conveniently at a high yield.

More specifically, the inventors, as a result of diligent study, found that "(±)-1-methyl-4-(2,4,6-trimethoxyphenyl)-3-piperidinone (3)" (also referred to as (±)-1-methyl-4-(2,4,6-trimethoxyphenyl)piperidin-3-one herein) can be manufactured near room temperature and at a high yield by reacting "(±)-1-methyl-4-(2,4,6-trimethoxyphenyl)piperidin-3-ol (1)" with a "sulfur trioxide complex (2)" in a suitable solvent. It was also found that "(R)-1-methyl-4-(2,4,6-trimethoxyphenyl)-3-piperidinone (+)-dibenzoyl-D-tartarate (5)" (also referred to as (R)-1-methyl-4-(2,4,6-trimethoxyphenyl)piperidin-3-one herein) can be obtained at an extremely high yield by adding an ether solvent upon dynamic kinetic resolution of (3) using "(+)-dibenzoyl-D-tartrate (4)". Further, a free form (6) of (5) is generally unstable. Meanwhile, it was found that a slurry of (5) can be stably handled by treating it with a base. It was also found that (6) can be reduced to "cis-(−)-flocinopiperidol (I)" with a surprisingly high selectivity by using a "sterically bulky reducing agent (7)".

[Chemical Formula 2]

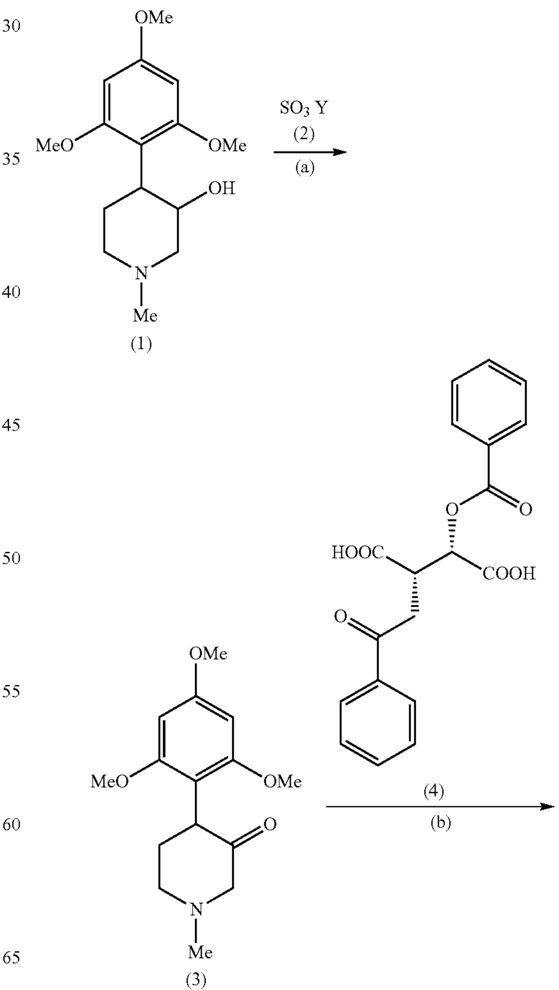

-continued

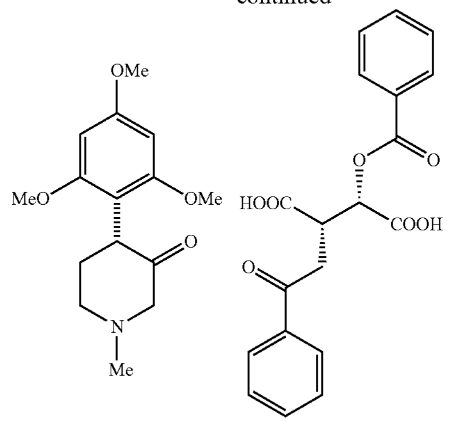

(5)

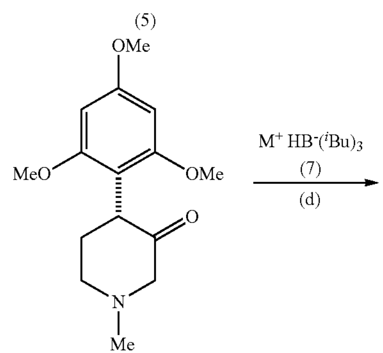

(6)

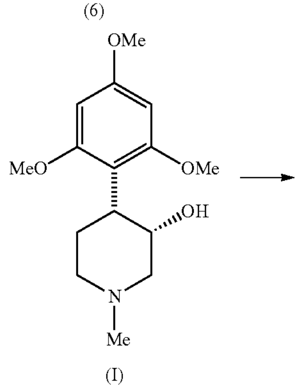

(I)

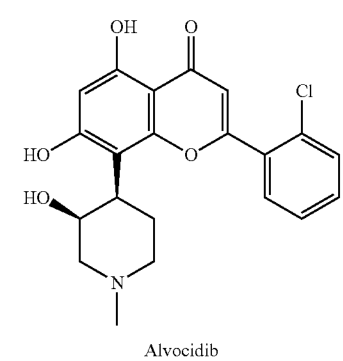

Alvocidib

Specifically, the present invention is the following.

[Item 1] A manufacturing method of cis-(−)-flocinopiperidol represented by formula (I):

[Chemical Formula 3]

(I)

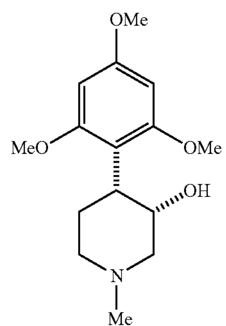

or a salt thereof or a solvate thereof, comprising the following step (d):

(d) reacting (R)-1-methyl-4-(2,4,6-trimethoxyphenyl)-3-piperidinone represented by formula (6):

[Chemical Formula 4]

(6)

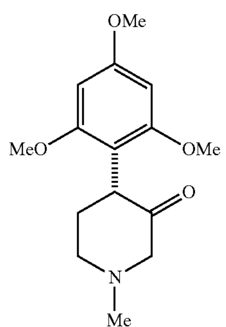

or a salt thereof or a solvate thereof with a compound of formula (7):

[Chemical Formula 5]

(7)

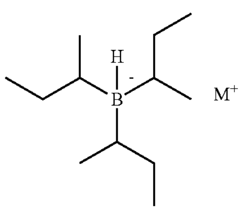

or a solvate thereof [wherein M is an alkali metal] in a solvent to manufacture cis-(−)-flocinopiperidol represented by formula (I):

[Chemical Formula 6]

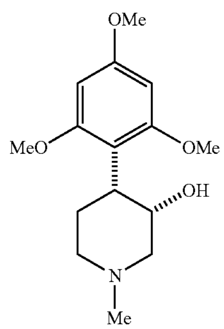

or a salt thereof or a solvate thereof.

[Item 2] The manufacturing method of item 1, wherein M in formula (7) used in step (d) is lithium, sodium, or potassium.

[Item 3] The manufacturing method of item 1 or 2, wherein M in formula (7) used in step (d) is lithium.

[Item 4] The manufacturing method of any one of items 1 to 3, wherein a compound of formula (I) or a solvate thereof is obtained in step (d) by extracting a product after a reduction reaction with an acidic aqueous solution and increasing the pH of the extraction solution.

[Item 5] The manufacturing method of any one of items 1 to 4, wherein a compound of formula (I) or a solvate thereof is obtained in step (d) by extracting a product after a reduction reaction with an acidic aqueous solution and dripping the extraction solution into a basic aqueous solution.

[Item 6] The manufacturing method of any one of items 1 to 5, wherein the pH of the acidic aqueous solution is 6.0 to 6.5 in step (d).

[Item 7] The manufacturing method of any one of items 1 to 6, wherein the pH of the acidic aqueous solution is 6.0 in step (d).

[Item 8] The manufacturing method of any one of items 1 to 7, further comprising the following step (c) before step (d):

(c) reacting (R)-1-methyl-4-(2,4,6-trimethoxyphenyl)-3-piperidinone (+)-dibenzoyl-D-tartrate represented by formula (5):

[Chemical Formula 7]

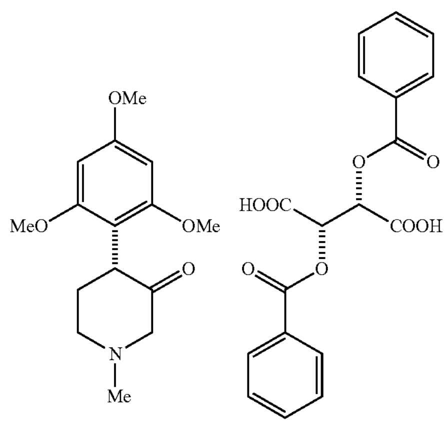

or a solvate thereof with a base in a solvent to manufacture (R)-1-methyl-4-(2,4,6-trimethoxyphenyl)-3-piperidinone represented by formula (6):

[Chemical Formula 8]

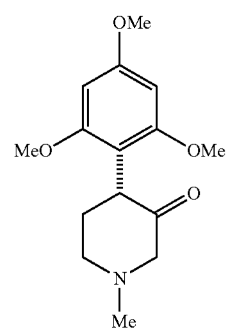

or a salt thereof or a solvate thereof.

[Item 9] The manufacturing method of any one of items 1 to 8, wherein the base used in step (c) is an organic base.

[Item 10] The manufacturing method of any one of items 1 to 9, wherein the base used in step (c) is a tertiary amine.

[Item 11] The manufacturing method of any one of items 1 to 10, wherein the solvent used in step (c) is an ether-based solvent.

[Item 12] The manufacturing method of any one of items 1 to 11, wherein step (d) is performed using a base-neutralized product in a state of a solution without isolation in step (c).

[Item 13] The manufacturing method of any one of items 1 to 12, further comprising the following step (b) before step (c):

(b) reacting (±)-1-methyl-4-(2,4,6-trimethoxyphenyl)-3-piperidinone represented by formula (3):

[Chemical Formula 9]

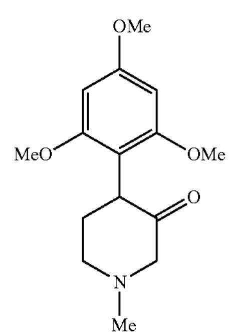

or a salt thereof or a solvate thereof with (+)-dibenzoyl-D-tartrate represented by formula (4):

[Chemical Formula 10]

(4)

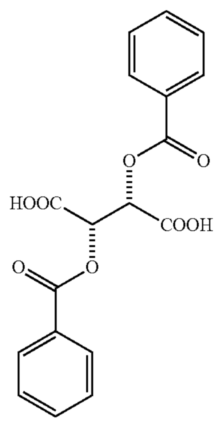

or a salt thereof or a solvate thereof in a reaction solvent to manufacture (R)-1-methyl-4-(2,4,6-trimethoxyphenyl)-3-piperidinone (+)-dibenzoyl-D-tartrate represented by formula (5):

[Chemical Formula 11]

(5)

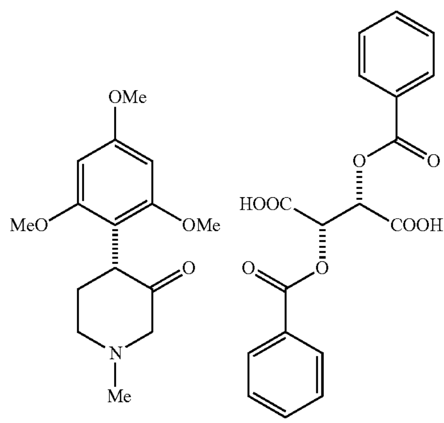

or a solvate thereof.

[Item 14] The manufacturing method of any one of items 1 to 13, wherein the reaction solvent in step (b) is at least one reaction solvent selected from an ester-based solvent, an ether-based solvent, an alcohol-based solvent, an amide-based solvent, a nitrile-based solvent, and an aromatic solvent.

[Item 15] The manufacturing method of any one of items 1 to 14, wherein the reaction solvent used in step (b) is an alcohol-based solvent.

[Item 16] The manufacturing method of any one of items 1 to 15, wherein a compound represented by formula (5) or a solvate thereof is precipitated by adding a poor solvent to a reaction solution after reacting (±)-1-methyl-4-(2,4,6-trimethoxyphenyl)-3-piperidinone represented by formula (3) or a salt thereof or a solvate thereof with a compound of formula (4) in step (b).

[Item 17] The manufacturing method of any one of items 1 to 16, wherein the poor solvent used in step (b) is at least one poor solvent selected from an ester-based solvent, an ether-based solvent, an alkane-based solvent, and an aromatic solvent.

[Item 18] The manufacturing method of any one of items 1 to 17, wherein the poor solvent used in step (b) is an ether-based solvent.

[Item 19] The manufacturing method of any one of items 1 to 18, further comprising the following step (a) before step (b):

(a) reacting (±)-1-methyl-4-(2,4,6-trimethoxyphenyl) piperidine-3-ol represented by formula (1):

[Chemical Formula 12]

(1)

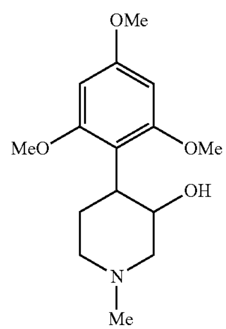

or a salt thereof or a solvate thereof with a compound represented by formula (2):

[Chemical Formula 13]

(2)

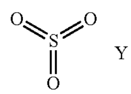

or a salt thereof or a solvate thereof [wherein Y is a 5- to 10-membered heteroaryl group, tertiary amine, or amide] and dialkyl sulfoxide to manufacture (±)-1-methyl-4-(2,4,6-trimethoxyphenyl)-3-piperidinone represented by formula (3):

[Chemical Formula 14]

(3)

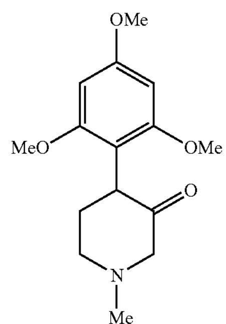

or a salt thereof or a solvate thereof.

[Item 20] The manufacturing method of any one of items 1 to 19, wherein Y in formula (2) used in step (a) is pyridine.

[Item 21] The manufacturing method of any one of items 1 to 20, wherein the reaction in step (a) is performed at a temperature of −10° C. or higher.

[Item 22] The manufacturing method of any one of items 1 to 21, wherein the reaction in step (a) is performed at a temperature from 0° C. to 30° C.

[Item 23] A manufacturing method of (R)-1-methyl-4-(2,4,6-trimethoxyphenyl)-3-piperidinone represented by formula (6):

[Chemical Formula 15]

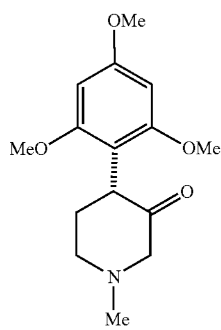

or a salt thereof or a solvate thereof, comprising the following step (c):

(c) reacting (R)-1-methyl-4-(2,4,6-trimethoxyphenyl)-3-piperidinone (+)-dibenzoyl-D-tartrate represented by formula (5):

[Chemical Formula 16]

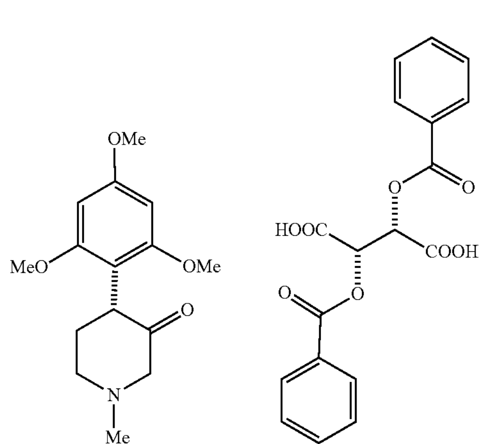

or a solvate thereof with a base in a solvent to manufacture (R)-1-methyl-4-(2,4,6-trimethoxyphenyl)-3-piperidinone represented by formula (6):

[Chemical Formula 17]

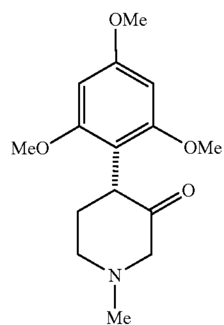

or a salt thereof or a solvate thereof.

[Item 24] The manufacturing method of item 23, wherein the base used in step (c) is an organic base.

[Item 25] The manufacturing method of item 23 or 24, wherein the base used in step (c) is a tertiary amine.

[Item 26] The manufacturing method of any one of items 23 to 25, wherein the solvent used in step (c) is an ether-based solvent.

[Item 27] A manufacturing method of (R)-1-methyl-4-(2,4,6-trimethoxyphenyl)-3-piperidinone (+)-dibenzoyl-D-tartrate represented by formula (5):

[Chemical Formula 18]

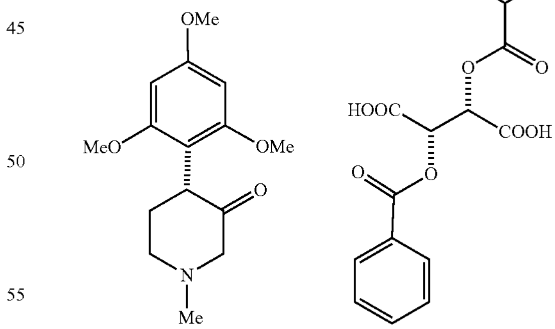

or a solvate thereof, comprising the following step (b):

(b) reacting (±)-1-methyl-4-(2,4,6-trimethoxyphenyl)-3-piperidinone represented by formula (3):

[Chemical Formula 19]

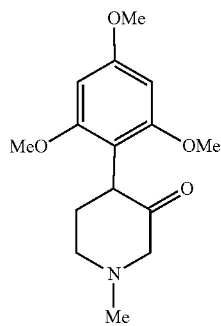

or a salt thereof or a solvate thereof with (+)-dibenzoyl-D-tartrate represented by formula (4):

[Chemical Formula 20]

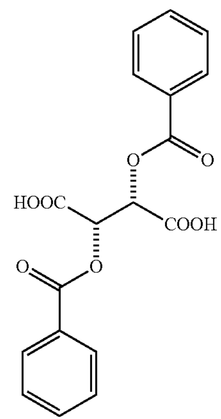

or a salt thereof or a solvate thereof in a reaction solvent to manufacture (R)-1-methyl-4-(2,4,6-trimethoxyphenyl)-3-piperidinone (+)-dibenzoyl-D-tartrate represented by formula (5):

[Chemical Formula 21]

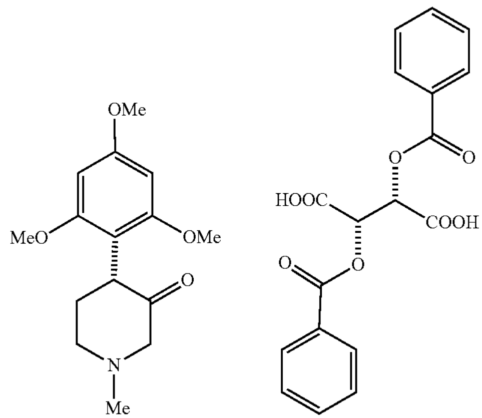

or a solvate thereof.

[Item 28] The manufacturing method of item 27, wherein the reaction solvent in step (b) is at least one reaction solvent selected from an ester-based solvent, an ether-based solvent, an alcohol-based solvent, an amide-based solvent, a nitrile-based solvent, and an aromatic solvent.

[Item 29] The manufacturing method of item 27 or 28, wherein the reaction solvent used in step (b) is an alcohol-based solvent.

[Item 30] The manufacturing method of any one of items 27 to 29, wherein a compound represented by formula (5) or a solvate thereof is precipitated by adding a poor solvent to a reaction solution after reacting (±)-1-methyl-4-(2,4,6-trimethoxyphenyl)-3-piperidinone represented by formula (3) or a salt thereof or a solvate thereof with a compound of formula (4) in step (b).

[Item 31] The manufacturing method of any one of items 27 to 30, wherein the poor solvent used in step (b) is at least one poor solvent selected from an ester-based solvent, an ether-based solvent, an alkane-based solvent, and an aromatic solvent.

[Item 32] The manufacturing method of any one of items 27 to 31, wherein the poor solvent used in step (b) is an ether-based solvent.

[Item 33] A manufacturing method of (±)-1-methyl-4-(2,4,6-trimethoxyphenyl)-3-piperidinone represented by formula (3):

[Chemical Formula 22]

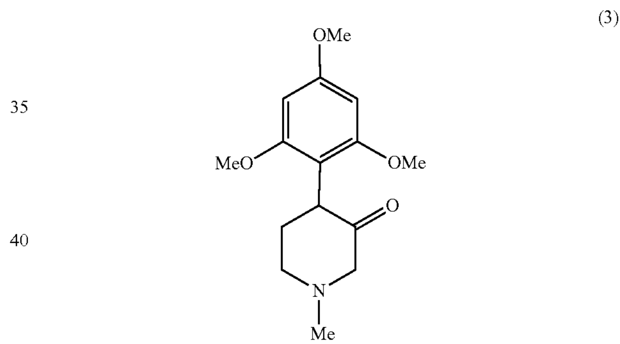

or a salt thereof or a solvate thereof, comprising the following step (a):

(a) reacting (±)-1-methyl-4-(2,4,6-trimethoxyphenyl) piperidine-3-ol represented by formula (1):

[Chemical Formula 23]

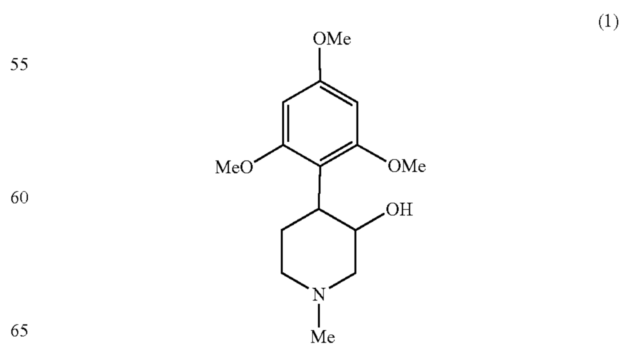

or a salt thereof or a solvate thereof with a compound represented by formula (2):

[Chemical Formula 24]

(2)

O O S O Y or a salt thereof or a solvate thereof [wherein Y is a 5- to 10-membered heteroaryl group, tertiary amine, or amide] and dialkyl sulfoxide to manufacture (±)-1-methyl-4-(2,4,6-trimethoxyphenyl)-3-piperidinone represented by formula (3):

[Chemical Formula 25]

(3)

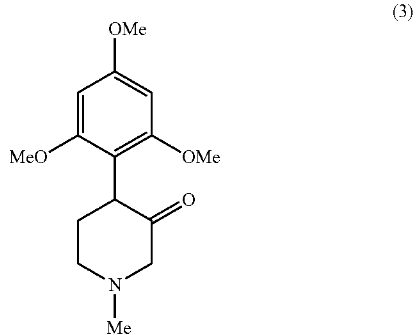

or a salt thereof or a solvate thereof.

[Item 34] The manufacturing method of item 33, wherein Y in formula (2) used in step (a) is pyridine.

[Item 35] The manufacturing method of item 33 or 34, wherein the reaction in step (a) is performed at a temperature of −10° C. or higher.

[Item 36] The manufacturing method of any one of items 33 to 35, wherein the reaction in step (a) is performed at a temperature from 0° C. to 30° C.

The present invention is intended so that one or more of the features described above can be provided not only as the explicitly disclosed combinations, but also as other combinations thereof. Additional embodiments and advantages of the present invention are recognized by those skilled in the art by reading and understanding the following detailed description as needed.

Advantageous Effects of Invention

The manufacturing method of the invention can manufacture cis-(−)-flocinopiperidol at a higher yield and higher purity with higher selectivity compared to known manufacturing methods and attains an effect such as high reproducibility, safety, cost-effectiveness, and convenience.

Since the present invention has a significantly higher selectivity of reduction that induces cis-(−)-flocinopiperidol compared to known manufacturing methods described in prior art documents, the present invention provides an industrially suitable method that can efficiently manufacture a product of interest without requiring purification by column chromatography (step (d)).

The present invention also has a higher yield from dynamic kinetic resolution compared to known manufacturing methods described in prior art documents without a need to isolate a free form after neutralization. Thus, the present invention can provide advantages such as simple operation (steps (b) and (c)).

In addition, oxidation of alcohol, which previously required ultralow temperatures near −60° C., can be performed near room temperature in a reaction of the present invention, so that a product can be manufactured more readily (step (a)).

DESCRIPTION OF EMBODIMENTS

The present invention is described hereinafter while showing the best mode thereof. Throughout the entire specification, a singular expression should be understood as encompassing the concept thereof in the plural form, unless specifically noted otherwise. Thus, singular articles (e.g., “a”, “an”, “the”, and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the disclosure pertains. In case of a contradiction, the present specification (including the definitions) takes precedence.

The terms that are used herein are described hereinafter.

As used herein, “solvate” refers to a complex formed by combining a compound with a solvent. Examples of solvates include hydrate, methanolate, ethanolate, and the like.

As used herein, “a compound, a salt thereof, or a solvate thereof” refers to the compound, a salt of the compound, a solvate of the compound, or a solvate of the salt of the compound.

As used herein, “ester solvent” refers to a solvent, which is a compound comprising one or more ester bonds in a molecule and is a liquid at a reaction temperature, having a property of dissolving or dispersing a reaction substrate.

Specific examples of “ester solvent” include methyl formate, ethyl formate, propyl formate, isopropyl formate, methyl acetate, ethyl acetate, propyl acetate, isopropyl acetate, n-butyl acetate, and isobutyl acetate. An ester solvent is preferably ethyl acetate or isopropyl acetate.

As used herein, “ether solvent” refers to a solvent, which is a compound comprising one or more ether bonds in a molecule and is a liquid at a reaction temperature, having a property of dissolving or dispersing a reaction substrate.

Specific examples of “ether solvent” include dimethyl ether, diethyl ether, diisopropyl ether, methyl tert-butyl ether, 1,2-dimethoxyethane, tetrahydrofuran, 2-methyltetrahydrofuran, and cyclopentyl methyl ether. An ether solvent is preferably methyl tert-butyl ether.

As used herein, “alcohol solvent” refers to a solvent, which is a compound comprising one or more hydroxyl groups in a molecule and is a liquid at a reaction temperature, having a property of dissolving or dispersing a reaction substrate.

Specific examples of “alcohol solvent” include methanol, ethanol, 1-propanol, 2-propanol, 1-butanol, 2-butanol, 3-methyl-1-butanol, 2-methyl-1-propanol, and tert-butyl alcohol. An alcohol solvent is preferably methanol.

As used herein, “amide solvent” refers to a solvent, which is a compound comprising one or more amide bonds in a molecule and is a liquid at a reaction temperature, having a property of dissolving or dispersing a reaction substrate.

Specific examples of "amide solvent" include N,N-dimethylacetamide, N,N-dimethylformamide, and N-methyl-2-pyrrolidone.

As used herein, "nitrile solvent" refers to a solvent, which is a compound comprising one or more cyano groups in a molecule and is a liquid at a reaction temperature, having a property of dissolving or dispersing a reaction substrate.

Specific examples of "nitrile solvent" include acetonitrile and propionitrile.

As used herein, "alkane solvent" refers to a solvent, which is a non-aromatic compound consisting of only carbon or hydrogen and is a liquid at a reaction temperature, having a property of dissolving or dispersing a reaction substrate.

Specific examples of "alkane solvent" include n-pentane, n-hexane, and n-heptane.

As used herein, "aromatic solvent" refers to a solvent, which is a compound comprising one or more benzene rings and is a liquid at a reaction temperature, having a property of dissolving or dispersing a reaction substrate.

Specific examples of "aromatic solvent" include toluene, xylene, and mesitylene.

As used herein, "dialkyl sulfoxide" is sulfoxide having two $C_{1-10}$ alkyl groups. Specific examples thereof include dimethyl sulfoxide, dibutyl sulfoxide, and dodecyl methyl sulfoxide. Dialkyl sulfoxide is preferably dimethyl sulfoxide.

As used herein, "5- to 10-membered heteroaryl group" includes a monocyclic 5- to 7-membered aromatic heterocyclic group ("5- to 7-membered heteroaryl group") and bicyclic 8- to 10-membered aromatic heterocyclic group ("8- to 10-membered heteroaryl group"), which comprise 1 to 4 atoms independently selected from the group consisting of a nitrogen atom, an oxygen atom, and a sulfur atom.

"5- to 10-membered heteroaryl group" is preferably a monocyclic 5- to 7-membered aromatic heterocyclic group ("5- to 7-membered heteroaryl group"), more preferably a 5- or 6-membered monocyclic aromatic heterocyclic group ("5- to 6-membered heteroaryl group"), and most preferably a 6-membered monocyclic aromatic heterocyclic group ("6-membered heteroaryl group").

Specific examples of "5- to 10-membered heteroaryl group" include a pyridyl group, pyridazinyl group, imidazolyl group, pyrimidinyl group, pyrazolyl group, oxazolyl group, isoxazolyl group, pyrazinyl group, triazinyl group, triazolyl group, tetrazolyl group, indolyl group, indazolyl group, quinolyl group, isoquinolyl group, benzimidazolyl group, quinoxalyl group, naphthyridinyl group, pyrrolo[3,2-c]pyridinyl group, pyrido[3,2-d]pyridinyl group, pyrido[3,2-d]pyrimidinyl group, imidazolo[4,5-c]pyridyl group, 2-oxo-1,2-dihydro-1,7-naphthyridinyl group, and the like.

"5- to 10-membered heteroaryl group" is preferably a pyridyl group, pyrimidinyl group, imidazolyl group, or pyridazinyl group, more preferably a pyridyl group, pyrimidinyl group, or imidazolyl group, still more preferably a pyridyl group or pyrimidinyl group, and most preferably a pyridyl group.

As used herein, "amide" is a compound comprising one or more amide bonds in a molecule and is preferably N,N-dimethylacetamide, N,N-dimethylformamide, or N-methyl-2-pyrrolidone, and more preferably N,N-dimethylformamide.

As used herein, "base" encompasses both inorganic bases and organic bases.

Specific examples of "inorganic base" include, but are not limited to, ammonium, lithium hydroxide, sodium hydroxide, calcium hydroxide, barium hydroxide, sodium carbonate, sodium hydrogen carbonate, potassium carbonate, cesium carbonate, mixtures thereof, and the like. An inorganic base is preferably lithium hydroxide, sodium hydroxide, sodium carbonate, potassium carbonate, or cesium carbonate, more preferably sodium carbonate, potassium carbonate, or cesium carbonate, and most preferably potassium carbonate or cesium carbonate.

Specific examples of "organic base" include triethylamine, N,N,N',N'-tetramethylethane-1,2-diamine, N,N-dimethylaniline, N,N-diisopropylethylamine, N-methylpyrrolidine, N-methylpiperidine, 1,4-diazabicyclo[2.2.2]octane, N-methylmorpholine, diazabicycloundecene, methylamine, diisopropylamine, pyrimidine, and pyridine. An organic base is more preferably triethylamine, diisopropylethylamine N,N,N',N'-tetramethylethane-1,2-diamine, 1,4-diazabicyclo[2.2.2]octane, N-methylpiperidine, pyrimidine, or pyridine, still more preferably N,N,N',N'-tetramethylethane-1,2-diamine, 1,4-diazabicyclo[2.2.2]octane, N-methylpiperidine, pyrimidine, or pyridine, and most preferably triethylamine.

Specific examples of "tertiary amine" include triethylamine, N,N-diisopropylethylamine, N-methylpyrrolidine, N-methylpiperidine, and N-methylmorpholine. Tertiary amine is more preferably triethylamine.

Specific examples of "acidic aqueous solution" include, but are not limited to, aqueous solutions of acetic acid, alginic acid, anthranilic acid, benzenesulfonic acid, benzoic acid, camphorsulfonic acid, citric acid, ethenesulfonic acid, formic acid, fumaric acid, furoic acid, gluconic acid, glutamic acid, glucorenic acid, galacturonic acid, glycidic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phenylacetic acid, propionic acid, phosphoric acid, salicylic acid, stearic acid, succinic acid, sulfanilic acid, sulfuric acid, tartaric acid, p-toluenesulfonic acid, potassium hydrogen sulfate, potassium dihydrogen phosphate, sodium dihydrogen phosphate, or the like. Preferred examples thereof include aqueous solutions of hydrochloric acid, hydrobromic acid, phosphoric acid, sulfuric acid, potassium hydrogen sulfate, potassium dihydrogen phosphate, or sodium dihydrogen phosphate.

Specific examples of "basic aqueous solution" include, but are not limited to, aqueous solutions of ammonium, lithium hydroxide, sodium hydroxide, potassium hydroxide, calcium hydroxide, barium hydroxide, sodium carbonate, sodium hydrogen carbonate, potassium carbonate, cesium carbonate, or mixtures thereof, and the like. Preferred examples thereof include aqueous solutions of lithium hydroxide, sodium hydroxide, potassium hydroxide, sodium carbonate, potassium carbonate, or cesium carbonate.

As used herein, acids that form a "salt" include, but are not limited to, acetic acid, alginic acid, anthranilic acid, benzenesulfonic acid, benzoic acid, camphorsulfonic acid, citric acid, ethenesulfonic acid, formic acid, fumaric acid, furoic acid, gluconic acid, glutamic acid, glucorenic acid, galacturonic acid, glycidic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phenylacetic acid, propionic acid, phosphoric acid, salicylic acid, stearic acid, succinic acid, sulfanilic acid, sulfuric acid, tartaric acid, p-toluenesulfonic acid, and the like.

Manufacturing methods of a compound of formula (I), optionally a salt thereof, or a solvate thereof according to the present invention are described below. (±)-1-methyl-4-(2,4,6-trimethoxyphenyl)piperidin-3-ol (1) can be manufactured by the method described in Patent Literature 2 or 3 or a method in accordance therewith, or by appropriately combining synthesis methods that are known to those skilled in the art.

While a compound obtained in each step can be used in a subsequent reaction directly as a reaction solution or as a mixture, the compound can also be isolated from a reaction mixture by a conventional method, and readily purified by separation means such as recrystallization, distillation, or chromatography.

Unless specifically noted otherwise, each symbol of compounds in the following reactions is synonymous with the descriptions above.

The methods of manufacturing a compound of the invention are described hereinafter with examples, but the present invention is not limited thereto.

Such manufacturing methods can be appropriately modified based on the expertise of those skilled in the art of organic synthetic chemistry. For the compounds used as a raw material, salts thereof can also be used in the following manufacturing methods, as long as the reaction is not adversely affected.

In the manufacturing methods described below, even if use of a protecting group is not specifically described, a functional group other than those at the reaction point can be protected as needed and deprotected after the completion of a reaction or after a series of reactions to obtain a compound of interest if one of the functional groups other than those at the reaction point is altered under the reaction condition or if it is unsuitable for post-reaction processing. Common protecting groups described in references (T. W. Greene and P. G. M. Wuts, "Protective Group in Organic Synthesis", 3$^{rd}$ Ed., John Wiley and Sons, Inc., New York (1999)) or the like can be used as the protecting groups used in these processes. A protecting group can be introduced or removed by a method that is commonly used in organic synthetic chemistry (e.g., method described in the aforementioned reference or the like) or a method in accordance therewith.

The starting material and intermediate in the manufacturing methods described below can be purchased as a commercially available product or are available by synthesis in accordance with a method described in a known document or a known method from a known compound. Salts or solvates of the starting material and intermediate can also be used, as long as the reaction is not adversely affected.

Manufacturing Method

[Chemical Formula 26]

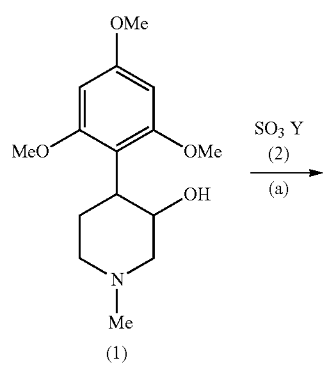

-continued

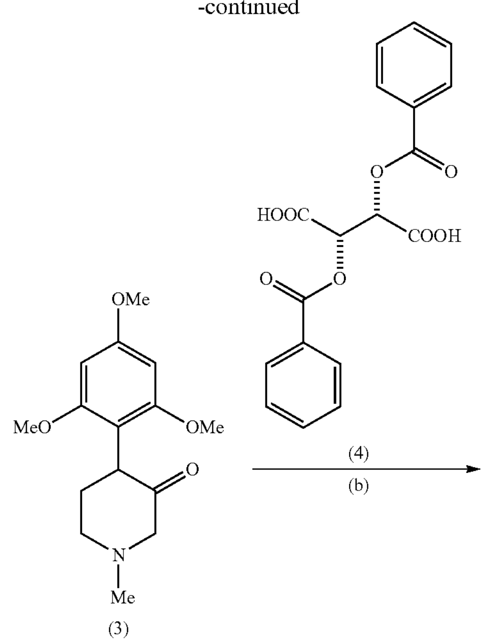

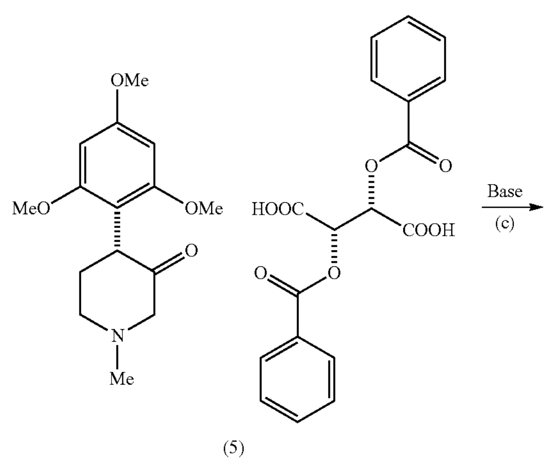

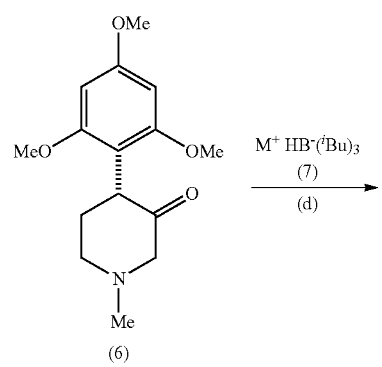

-continued

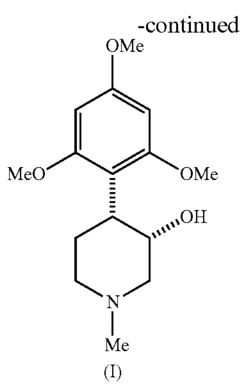

(I)

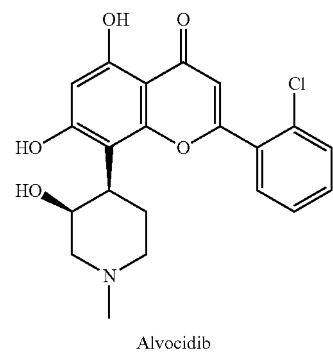

Alvocidib

As described below, step (d) for reducing a cyclic ketone with a cis-selective substitution at position a is one of the most important features of the method of the invention, but steps (a), (b), and (c) are also important features of the invention. While steps (a), (b), (c), and (d) are described with the following preferred embodiments, the present invention is not limited thereto.

Step (a)

[Chemical Formula 27]

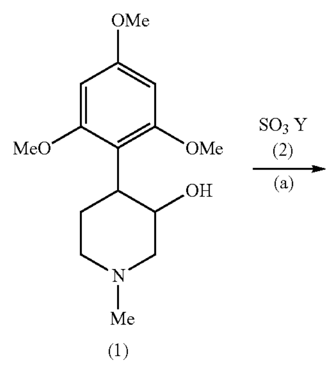

wherein Y is a 5- to 10-membered heteroaryl group, tertiary amine, or amide.

For (±)-1-methyl-4-(2,4,6-trimethoxyphenyl)piperidin-3-ol represented by formula (1), a commercially available product can be used, or the compound can be manufactured by a method described in various documents. For example, the compound can be manufactured by the method described in Patent Literature 2.

For a sulfur trioxide complex represented by formula (2), a commercially available product can be used, or the complex can be manufactured by a method described in various documents. For example, the complex can be manufactured by the method described in D. C. Akwaboah, et al., Org. Lett. 19, 1180 (2017).

This is a step for obtaining (±)-1-methyl-4-(2,4,6-trimethoxyphenyl)-3-piperidinone represented by formula (3) by reacting (±)-1-methyl-4-(2,4,6-trimethoxyphenyl)piperidin-3-ol represented by formula (1) with a sulfur trioxide complex represented by formula (2) and dialkylsulfoxide in a solvent or without a solvent.

Examples of dialkyl sulfoxide used in this step include dimethyl sulfoxide, dibutyl sulfoxide, and dodecyl methyl sulfoxide. Dialkyl sulfoxide is preferably dimethyl sulfoxide. The solvent used in this step can be dichloromethane, but dialkyl sulfoxide can also be used as the solvent.

The amount of compound represented by formula (2) used is generally 0.8 equivalent to 10 equivalent, and preferably 2.5 equivalent to 3.5 equivalent with respect to 1 equivalent of a compound represented by formula (1).

The amount of dialkyl sulfoxide used is generally 0.8 equivalent to 10 equivalent, and preferably 6 equivalent to equivalent with respect to 1 equivalent of a compound represented by formula (1).

The reaction time is generally about 1 hour to 12 hours, and preferably 2 hours to 4 hours.

The reaction temperature is generally −10° C. to 50° C., and preferably 10° C. to 30° C.

Step (b)

[Chemical Formula 28]

-continued

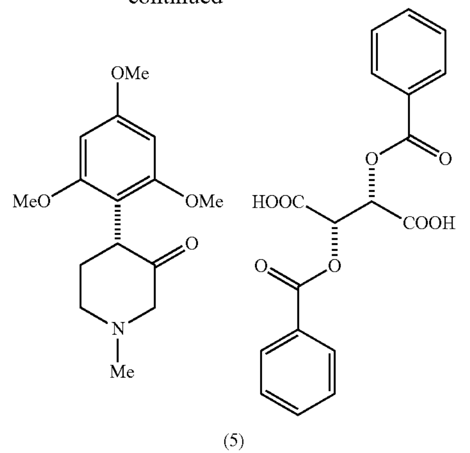

(5)

For (+)-dibenzoyl-D-tartrate represented by formula (4), a commercially available product can be used.

This is a step for obtaining only (R)-1-methyl-4-(2,4,6-trimethoxyphenyl)-3-piperidinone (+)-dibenzoyl-D-tartrate represented by formula (5) (compound having a specific stereostructure with respect to (+)-dibenzoyl-D-tartrate) by dynamic kinetic resolution of a racemic compound for (±)-1-methyl-4-(2,4,6-trimethoxyphenyl)-3-piperidinone represented by formula (3) manufactured in manufacturing step (a) described above by using (+)-dibenzoyl-D-tartrate represented by formula (4) in a reaction solvent. The solvent used in the chemical reaction of step (b) is referred to as a "reaction solvent" herein. Any solvent can be used as the reaction solvent, as long as the solvent facilitates the progression of the reaction in step (b).

The reaction solvent can be, for example, at least one solvent selected from an ester solvent, ether solvent, alcohol solvent, amide solvent, nitrile solvent, and aromatic solvent. The reaction solvent used in this reaction is preferably an alcohol solvent, and more preferably methanol.

It is desirable in this reaction to react (±)-1-methyl-4-(2,4,6-trimethoxyphenyl)-3-piperidinone represented by formula (3) or a salt thereof or a solvate thereof with a compound of formula (4) and then add a poor solvent to the reaction solution to induce elution of a compound represented by formula (5) or a solvate thereof. "Poor solvent" is a solvent with which the solubility of a product of interest into a mixture of a reaction solution and the poor solvent prepared from adding the poor solvent to the reaction mixture is lower than the solubility of the product of interest into the reaction mixture. Those skilled in the art can appropriately select a poor solvent that is suitable for the reaction solvent to be used by referring to the descriptions herein and known technologies. A poor solvent can be at least one poor solvent selected from an ester solvent, ether solvent, alkane solvent, and aromatic solvent. A poor solvent is preferably an ether solvent and more preferably methyl tert-butyl ether.

The amount of compound represented by formula (4) used is generally 0.8 equivalent to 10 equivalent, and preferably 1 equivalent to 1.5 equivalent with respect to 1 equivalent of a compound represented by formula (3).

The reaction time is generally about 10 minutes to 10 hours, and preferably 30 minutes to 2 hours.

The reaction temperature is generally −10° C. to 100° C., and preferably 40° C. to 60° C.

Step (c)

[Chemical Formula 29]

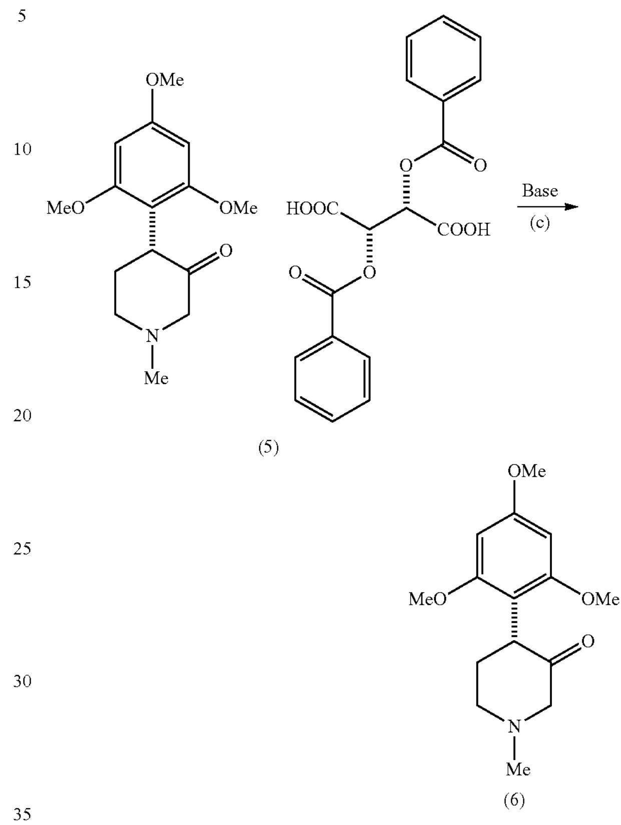

This is a step for treating the (R)-1-methyl-4-(2,4,6-trimethoxyphenyl)-3-piperidinone (+)-dibenzoyl-D-tartrate represented by formula (5) obtained in step (b) described above with a base. Such a base treatment removes tartaric acid, such that (R)-1-methyl-4-(2,4,6-trimethoxyphenyl)-3-piperidinone represented by formula (6) would be generated in the system.

The base used in this step is preferably an organic base, more preferably tertiary amine, still more preferably triethylamine, N,N-diisopropylethylamine, N-methylpyrrolidine, N-methylpiperidine, or N-methylmorpholine, and most preferably triethylamine.

The solvent used in this reaction is an ester solvent, ether solvent, alcohol solvent, amide solvent, nitrile solvent, or aromatic solvent, more preferably an ether solvent, and still more preferably 1,2-dimethoxyethane and/or tetrahydrofuran.

This reaction is preferably characterized by being performed consecutively with step (d). In such a case, step (d) is performed without isolating a compound represented by formula (6).

The amount of base used is generally 1 equivalent to 10 equivalent, and preferably 3 equivalent to 5 equivalent with respect to 1 equivalent of a compound represented by formula (5).

The reaction time is generally about 10 minutes to 10 hours, and preferably 20 minutes to 1 hour.

The reaction temperature is generally −10° C. to 50° C., and preferably 10° C. to 25° C.

Step (d)

[Chemical Formula 30]

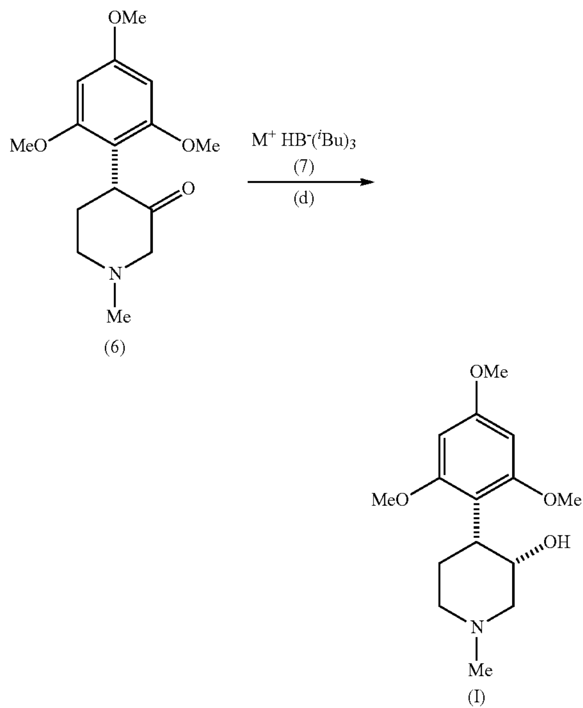

This is a step for obtaining cis-(−)-flocinopiperidol represented by formula (1) by reducing (R)-1-methyl-4-(2,4,6-trimethoxyphenyl)-3-piperidinone represented by formula (6) obtained in step (c) described above using a triisobutylborohydride represented by formula (7) in a solvent.

The amount of triisobutylborohydride represented by formula (7) used is generally 1 equivalent to 10 equivalent, and preferably 1.5 equivalent to 3 equivalent with respect to 1 equivalent of a compound represented by formula (6). Triisobutylborohydride is preferably sodium triisobutylborohydride, potassium triisobutylborohydride, or lithium triisobutylborohydride, and more preferably lithium triisobutylborohydride. Specifically, alkali metal M according to formula (7) is preferably lithium, sodium, or potassium, and more preferably lithium.

The solvent used in this reaction is preferably an ether solvent or aromatic solvent, preferably an ether solvent, and more preferably 1,2-dimethoxyethane and/or tetrahydrofuran. The reaction time is generally about 10 minutes to 10 hours, and preferably 1 hour to 3 hours.

The reaction temperature is generally −10° C. to 50° C., and preferably −5° C. to 15° C.

Post-processing associated with this reaction is preferably characterized by extracting a post-reduction reaction product with an acidic aqueous solution and raising the pH of the extracted solution (e.g., adding the extracted solution dropwise to a basic aqueous solution) to obtain a compound represented by formula (I). The pH of an acidic aqueous solution is preferably 5.5 to 6.5, and more preferably 6.0 to 6.4. A basic aqueous solution is preferably an aqueous lithium hydroxide solution, aqueous sodium hydroxide solution, aqueous potassium hydroxide solution, aqueous sodium carbonate solution, aqueous potassium carbonate solution, aqueous cesium carbonate solution, or aqueous sodium hydrogen carbonate solution, preferably an aqueous lithium hydroxide solution, aqueous sodium hydroxide solution, or aqueous potassium hydroxide solution, more preferably an aqueous 3 to 20% potassium hydroxide solution, and most preferably an aqueous 5 to 10% potassium hydroxide solution.

cis-(−)-Flocinopiperidol can be manufactured cost effectively and safely at a high purity and high yield by the manufacturing method (d) of the invention. Each intermediate can be manufactured cost effectively, safely, and conveniently by performing steps (a), (b), and (c) from a starting material.

The compound of formula (1) is a known substance, which can be readily synthesized in accordance with a method in a known document. A compound of formula (3) can be manufactured cost effectively, safely, and conveniently at a high yield and high purity by performing step (a) in dimethyl sulfoxide in the presence of a sulfur trioxide-pyridine complex by using said compound. While ultralow temperature such as −60° C. is required in commonly used Swern oxidation, this reaction can be performed near room temperature, which is extremely useful for manufacturing.

A crystal of a compound of formula (5) can be manufactured cost effectively, safely, and conveniently at a high yield and high purity by adding methyl tert-butyl ether (MTBE) after performing step (b) for forming a salt from a compound of formula (3) and a compound of formula (4) in methanol. The methods in known documents obtained a second crystal from the post-crystallization filtrate, but this reaction can manufacture a crystal at a high yield from obtaining only a first crystal. The operation is more convenient and useful for manufacturing.

An ether solution of formula (6) can be manufactured cost effectively, safely, and conveniently at a high yield and high purity by performing step (c) in a mixture of 1,2-dimethoxyethane (DME) and tetrahydrofuran (THF) by using a compound of formula (5) and triethylamine as a base. A compound of formula (6) can be readily converted into a racemate, but a compound of formula (6) can be obtained at a high optical purity without forming a racemate in this reaction.

cis-(−)-Flocinopiperidol can be manufactured at a high yield, with high selectivity, and at high purity by performing step (d) in an ether solvent by using an ether solution of a compound of formula (6) and lithium triisobutylborohydride. Cis/trans selectivity of cis-(−)-flocinopiperidol is about 7/3 in a method of a known document such as Non Patent Literature 1, but this reaction surprisingly exhibits selectivity of 99.8/0.2. For this reason, purification is facilitated, and purification by silica gel chromatography is not required, which are extremely useful for manufacturing.

The order of adding reagents or the like is not limited to the order described above.

EXAMPLE

The present invention is described in further detail hereinafter with Reference Examples and Examples, but the present invention is not limited thereby. Compounds were identified with an elemental analysis value, a mass spectrum, a high performance liquid chromatography mass spectrometer (LCMS), NMR spectra, high performance liquid chromatography (HPLC), or the like.

The measurement conditions for high performance liquid chromatography (HPLC) are described below. The retention time is indicated by Rt (minutes). The measurement conditions used for measurement are described in each of the actual measurement values. In the following description, HPLC purity (area %) calculates the purity by comparing each peak area by using one of the following measurement conditions.

Method A

Column: Kinetex 1.7 um C18 100A (100×2.1 mm)

Eluent: solution A: aqueous 0.01 mol/l disodium hydrogen phosphate solution, solution B: acetonitrile Gradient Condition:

TABLE 1

| Minutes | A (%) | B (%) |
|---|---|---|
| 0 | 10 | 90 |
| 12.5 | 76.7 | 23.3 |
| 12.51 | 95 | 5 |
| 15 | 95 | 5 |
| 15.01 | 10 | 90 |
| 20 | 10 | 90 |

Flow rate: 1.2 mL/min

Column temperature: 40° C.

Wavelength: 230 nm

Rt of 1-methyl-4-(2,4,6-trimethoxyphenyl)piperidin-3-ol measured by method A is shown in the following table.

TABLE 2

| Compound | Rt (minutes) |
|---|---|
| 1-methy1-4-(2,4,6-trimethoxyphenyl)piperidin-3-ol | 11.7 |

Method B

Column: Kinetex 1.7 um C18 100A (100×2.1 mm)

Eluent: solution A: aqueous 0.05% trifluoroacetic acid solution, solution B: acetonitrile (0.05% trifluoroacetic acid)

Gradient Condition:

TABLE 3

| Minutes | A (%) | B (%) |
|---|---|---|
| 0 | 95 | 5 |
| 15 | 50 | 50 |
| 18 | 10 | 90 |
| 23 | 10 | 90 |
| 23.01 | 95 | 5 |
| 28 | 95 | 5 |

Flow rate: 0.3 mL/min

Column temperature: 40° C.

Wavelength: 220 nm

Rt of 1-methyl-4-(2,4,6-trimethoxyphenyl)piperidin-3-one, (R)-1-methyl-4-(2,4,6-trimethoxyphenyl)piperidin-3-one, and cis-(−)-flocinopiperidol measured by method B is shown in the following table.

TABLE 4

| Compound | Rt (minutes) |
|---|---|
| 1-methy1-4-(2,4,6-trimethoxyphenyl)piperidin-3-one | 8.8 |
| (R)-1-methy1-4-(2,4,6-trimethoxyphenyl)piperidin-3-one | 8.8 |
| cis-(−)-flocinopiperidol | 9.2 |

Method C

Column: Chiralpak AD 5 um (250×4.6 mm)

Eluent: heptane/2-propanol/triethylamine: 80/20/0.02

Flow rate: 0.5 mL/min

Column temperature: 40° C.

Wavelength: 235 nm

Rt of 1-methyl-4-(2,4,6-trimethoxyphenyl)piperidin-3-one, (R)-1-methyl-4-(2,4,6-trimethoxyphenyl)piperidin-3-one, and cis-(−)-flocinopiperidol measured by method C is shown in the following table.

TABLE 5

| Compound | Rt (minutes) |
|---|---|
| 1-methy1-4-(2,4,6- | 13.4 |
| trimethoxyphenyl)piperidin-3-one | 14.9 |
| (R)-1-methy1-4-(2,4,6- | 14.9 |
| trimethoxyphenyl)piperidin-3-one | |
| cis-(−)-flocinopiperidol | 17.6 |

The following abbreviations may be used in the Examples and Tables in the Examples to simplify the descriptions herein.

MTBE: methyl tert-butyl ether

DME: 1,2-dimethoxyethane

THF: tetrahydrofuran

DBU: 1,8-diazabicyclo[5.4.0]-7-undecene

DMF: N,N-dimethylformamide

MEK: methyl ethyl ketone

DMSO: dimethylsulfoxide $CDCl_3$: deuterated chloroform

MeOH: methanol min: minutes

As symbols used in NMR, 5 refers to a chemical shift value, s refers to singlet, d refers to doublet, t refers to triplet, q refers to quartet, m refers to multiplet, and J refers to a spin coupling constant.

While the present invention is described in more detail hereinafter with Examples and Reference Examples, the technical scope of the present invention is not limited to such Examples. The present invention may be altered to the extent that the altered invention remains within the scope of the present invention. It should be noted that compound names in the following Examples and Comparative Examples do not necessarily follow the IUPAC nomenclature.

Example 1: Manufacturing method of (±)-1-methyl-4-(2,4,6-trimethoxyphenyl)piperidin-3-one

[Chemical Formula 31]

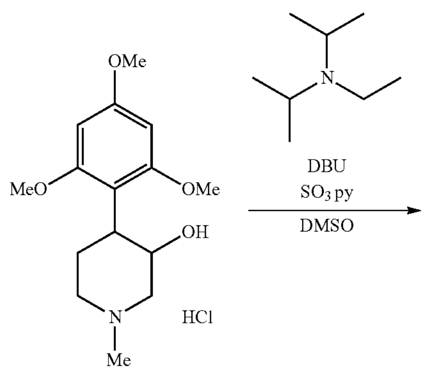

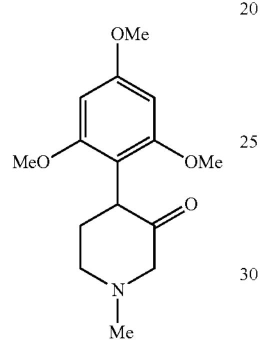

Under a nitrogen atmosphere, a sulfur trioxide-pyridine complex (52.6 g) was dissolved at 30° C. in dimethyl sulfoxide (172 g), and the mixture was cooled to 15° C. Under a nitrogen atmosphere in another container, (±)-1-methyl-4-(2,4,6-trimethoxyphenyl)piperidin-3-ol hydrochloride (35 g) was suspended in dimethyl sulfoxide (55.9 g). Diisopropylethylamine (56.9 g) was added dropwise while being maintained at 20° C., and then DBU (16.77 g) was added dropwise at 20° C. The aforementioned dimethyl sulfoxide solution of a sulfur trioxide-pyridine complex was added dropwise to the suspension while maintaining the internal temperature at 20° C. The resulting solution was stirred for 2 hours at 20° C. Cooled toluene (210 g) was added dropwise at 20° C., and the resulting solution was cooled to 10° C. After adding water (245 g) dropwise at 10° C., the mixture was warmed to 25° C. After separating the solution, the aqueous layer in the bottom layer was extracted twice with toluene (105 g) and combined with the separated top layer. The organic layer was then washed twice with saturated saline (140 g), with saturated ammonium chloride water (70 g), and with water (35 g). Toluene (105 g) was added, and the content was concentrated to 96 g. MTBE (280 g) was added, and the content was concentrated to 98 g. MTBE (280 g) was added, and the content was concentrated to 95 g. MTBE (280 g) was added, and the content was concentrated to 91 g. The residue was warmed to 55° C. Acetonitrile (10.5 g) was added, and heptane (65 g) was added dropwise at 55° C. After cooling to 30° C., a small amount of 1-methyl-4-(2,4,6-trimethoxyphenyl)piperidin-3-one was added, and the mixture was stirred at 30° C. The mixture was again warmed to 55° C. and then filtered. The filtrate was cooled to 30° C. A small amount of 1-methyl-4-(2,4,6-trimethoxyphenyl)piperidin-3-one was added again, and the mixture was cooled to 0° C. Heptane (65 g) was added, and the precipitate was filtered out. The precipitate was washed with a mixture of MTBE and heptane and then dried to obtain (±)-1-methyl-4-(2,4,6-trimethoxyphenyl)piperidin-3-one (18.5 g, yield: 60%, HPLC area %: 95.3 area %).

$^1$H-NMR (400 MHz, $CDCl_3$) δ: 1.90-1.97 (m, 1H), 2.33 (s, 1H), 2.38 (s, 3H), 2.45-2.52 (m, 1H), 2.81 (d, J=16.0 Hz, 1H), 2.89 (d, J=11.6 Hz, 1H), 3.44 (d, J=15.6 Hz, 1H), 3.73 (s, 6H), 3.78 (s, 3H), 3.87 (dd, J=11.8, 7.4 Hz, 1H), 6.12 (s, 2H)

The manufacturing method of Example 1 can perform a reaction closer to room temperature and is better for industrial use in comparison to the methods of Patent Literatures 2 and 3 and Non Patent Literature 2. Said manufacturing method is better than Patent Literature 3 in that purification by silica gel column chromatography is not required.

Example 2: Manufacturing Method of (R)-1-methyl-4-(2,4,6-trimethoxyphenyl)piperidin-3-one (+)-dibenzoyl-D-tartrate

[Chemical Formula 32]

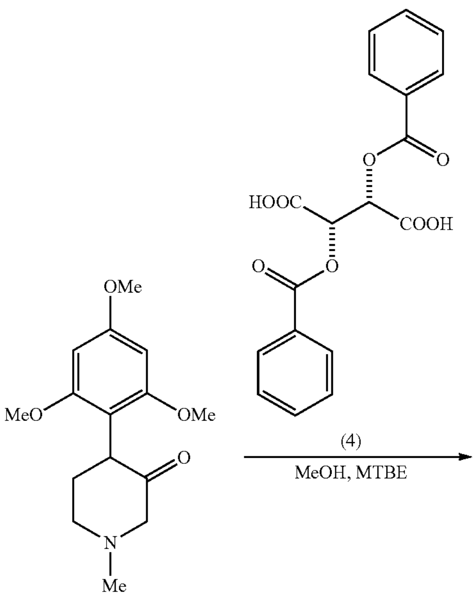

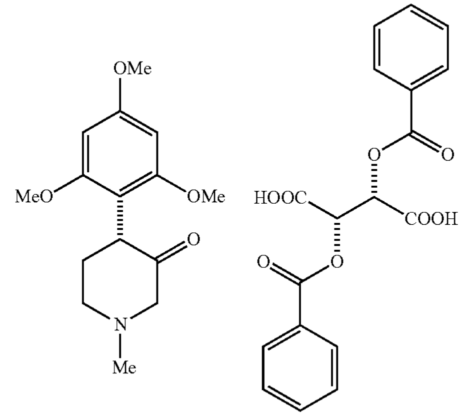

Under a nitrogen atmosphere, (±)-1-methyl-4-(2,4,6-trimethoxyphenyl)piperidin-3-one (500 g) and (+)-dibenzoyl-D-tartrate (352.7 g) were dissolved in methanol (1750 g) at room temperature. The mixture was warmed to 50° C. A methanol (500 g) solution of (+)-dibenzoyl-D-tartrate (352.7 g) was added dropwise over 30 minutes at 50° C. The mixture was incubated and stirred for 1 hour. MTBE (2250 g) was added dropwise at 50° C. The mixture was warmed to 55° C. thereafter. The mixture was incubated and stirred for 5 hours. The mixture was cooled to 20° C., incubated and stirred overnight. The precipitate was filtered out. The precipitate was washed twice with a mixture of methanol (500 g) and MTBE (500 g), washed twice with MTBE (1000 g), and then dried to obtain (R)-1-methyl-4-(2,4,6-trimethoxyphenyl)piperidin-3-one (+)-dibenzoyl-D-tartrate (901.2 g, yield: 79%, HPLC purity: 41.84 area %, HPLC area % of (+)-dibenzoyl-D-tartrate: 57.64 area %).

$^{1}$H-NMR (400 MHz, DMSO-d6) δ: 1.80-1.85 (m, 1H), 2.18-2.28 (m, 1H), 2.46 (s, 3H), 2.71-2.79 (m, 1H), 3.05-3.09 (m, 1H), 3.15-3.19 (m, 1H), 3.43-3.48 (m, 1H), 3.70 (s, 6H), 3.76 (s, 3H), 3.83 (dd, J=12.0 Hz, 6.8 Hz, 1H), 5.79 (s, 2H), 6.22 (s, 2H), 7.56 (dd, J=7.8, 7.8 Hz, 4H), 7.70 (dd, J=7.4 Hz, 7.4 Hz, 2H), 7.98 (d, J=7.6 Hz)

The manufacturing method of Example 2 is better than Patent Literature 1 and Non Patent Literature 1 in terms of reproducibility. The method can also achieve a yield of 79% from a single crystallization and thus has excellent usability. The method is better than Patent Literature 2 and Non Patent literature 2 in terms of yield in view of the lack of production of unwanted enantiomers. The usability is also excellent because unwanted enantiomers do not need to be removed.

Example 3: Treatment of (R)-1-methyl-4-(2,4,6-trimethoxyphenyl)piperidin-3-one (+)-dibenzoyl-D-tartrate with a Base

[Chemical Formula 33]

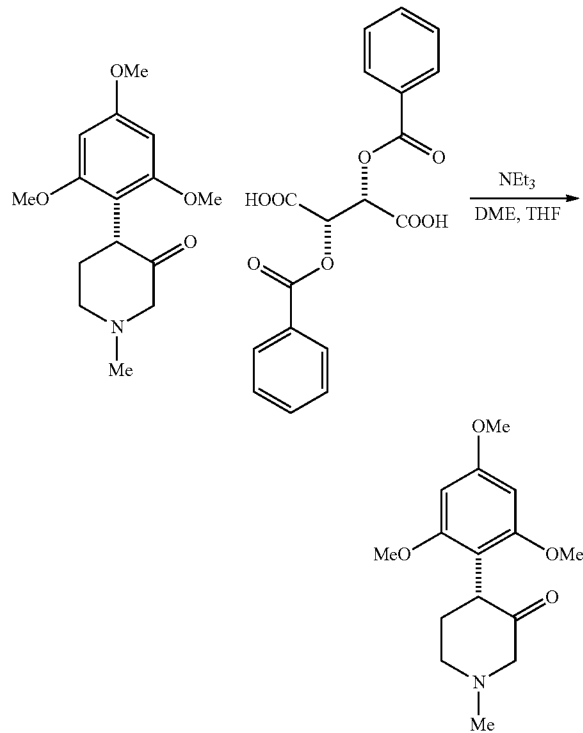

(R)-1-methyl-4-(2,4,6-trimethoxyphenyl)piperidin-3-one (+)-dibenzoyl-D-tartrate (400 g) was dried for 8 hours at 50° C. and then cooled to 5° C. under reduced pressure within a reaction vessel. DME (2000 g) and THF (2000 g) were added, and triethylamine (253.9 g) was added dropwise at an internal temperature of 5° C. The mixture was then warmed to 18° C., and incubated and stirred for 30 minutes. The precipitate was removed by filtration and washed twice with THF (240 g). The filtrate was combined with the washing solution (4461 g, yield: 100%, HPLC purity: 97.55 area %, optical purity: 99.36% ee). The solution was used in the next step without purification.

Treatment with a base in Example 3 is better than Patent Literatures 1 and 2 and Non Patent Literatures 1 and in that it is not necessary to isolate relatively unstable products. Such treatment is also better in terms of the ability to suppress racemate formation by using triethylamine. The treatment is better than Patent Literature 2 and Non Patent Literature 2 in terms of the ability to suppress racemate formation.

Example 4: Manufacturing Method of cis-(−)-flocinopiperidol

[Chemical Formula 34]

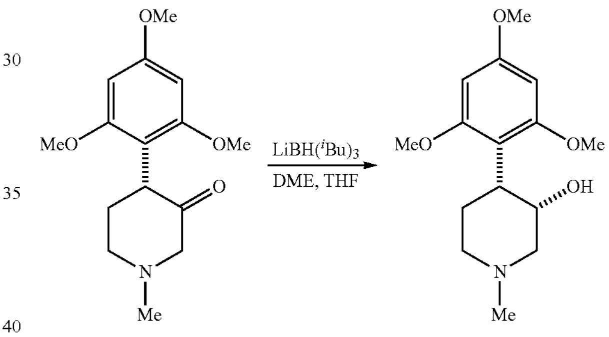

Under a nitrogen atmosphere, a THF solution (1210.6 g) of lithium triisobutylborohydride was cooled to 0° C. The solution obtained in Example 3 (4461.0 g) was added dropwise at an internal temperature of 0° C. The mixture was incubated and stirred for 2 hours at 0° C. The solution was added dropwise at 10° C. or lower to an aqueous 15% potassium hydroxide solution (1875 g) cooled to 5° C. After the addition, the mixture was warmed to 15° C., and 30% hydrogen peroxide water (426.7 g) was added dropwise at an internal temperature of 30° C. or lower. After stirring for 30 minutes at 20° C., an aqueous 24% sodium hydrogen sulfite solution (413.55 g) was added dropwise at 20° C., and the mixture was stirred for 1 hour. The mixture was checked for peroxides with potassium iodide-starch paper, and toluene (1752 g) was added. After 10 minutes of stirring, the aqueous layer was removed, and the organic layer (7403 g) was concentrated under reduced pressure to 2802 g. Toluene (1752 g) was added again, and concentrated under reduced pressure to 958 g. Toluene (1456 g) was added. An aqueous 5% potassium dihydrogen phosphate solution (525.7 g) was added at 20° C. The pH was adjusted to 6.37 with concentrated hydrochloric acid (56 g). A portion of the post-separation bottom layer (37.2 g) was added dropwise at 20° C. to an aqueous 7% potassium hydroxide solution (876 g), and cis-(−)-flocinopiperidol (0.88 g) was added. The remainder of the post-separation bottom layer (710.1 g) was added dropwise at 20° C. The mixture was incubated and stirred for 2 hours at 20° C. The precipitate was filtered out, washed twice with water (200 g) and then dried to obtain cis-(−)-flocinopiperidol (156.4 g, yield: 88.6%, HPLC purity: 99.91 area %, optical purity: 99.3% ee).

$^1$H-NMR (400 MHz, $CDCl_3$) δ: 1.37-1.42 (m, 1H), 1.65 (s, 3H), 2.04 (ddd, J=11.6, 11.6, 2.7 Hz, 1H), 2.12-2.15 (m, 1H), 2.31 (s, 3H), 2.83-2.94 (m, 1H), 2.96-3.02 (m, 2H), 3.34-3.39 (m, 1H), 3.81 (s, 9H), 3.84-3.85 (m, 1H), 6.17 (s, 2H)

The manufacturing method of Example 4 is better than Patent Literature 1 and Non Patent Literature 1 in terms of yield and cis-selectivity. The method is also better in terms of usability such as the reaction temperature of 0° C., thus no need of ultralow temperatures, and the ability to purify without using column chromatography. The method is also better than Patent Literatures 2 and 3 and Non Patent Literature 2 in terms of the yield of a reducing reaction.

cis-(−)-Flocinopiperidol can be industrially manufactured at a high efficiency, with high selectively, and at a high purity by using the manufacturing methods of Examples 1 to 4 according to the invention of the present application.

For comparison with the manufacturing methods according to the invention of the present application, (±)-1-methyl-4-(2,4,6-trimethoxyphenyl)piperidin-3-one was manufactured below through Swern oxidation (Reference Example 1). (R)-1-methyl-4-(2,4,6-trimethoxyphenyl)piperidin-3-one (+)-dibenzoyl-D-tartrate was also manufactured through optical resolution (Reference Example 2).

Reference Example 1: Manufacturing Method of (±)-1-methyl-4-(2,4,6-trimethoxyphenyl)piperidin-3-one hydrochloride

[Chemical Formula 35]

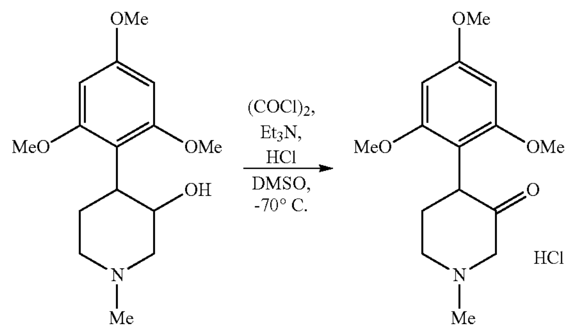

Under a nitrogen atmosphere, oxalyl chloride (13.8 g) was dissolved into methylene chloride (150 g), and the mixture was cooled to −78° C. A methylene chloride (100 g) solution of dimethyl sulfoxide (18.95 g) was added dropwise over 30 minutes to this solution at −70° C. The mixture was stirred for 15 minutes at −70° C. A solution of methylene chloride (75 g) of (±)-1-methyl-4-(2,4,6-trimethoxyphenyl)piperidin-3-one (25 g) was added dropwise in 25 minutes to this solution at −70° C. The solution was stirred for 1 hour at −78° C. Triethylamine (40.9 g) was added dropwise in 30 minutes at −78° C. and stirred for 30 minutes. The mixture was warmed to −20° C., and saturated sodium bicarbonate water (250 g) was added dropwise in 30 minutes. Water (250 g) was added, and extraction was performed twice with toluene (250 ml). The organic layer was combined. Saturated saline (100 ml) was added. After separation of the solution, the organic layer was dried with sodium sulfate. After filtration and then concentration under reduced pressure, the residue was dissolved in ethyl acetate (100 g). Insoluble matters were filtered out. 4N hydrochloric acid/ethyl acetate (30 ml) was added dropwise to the filtrate and the mixture was stirred at room temperature. The precipitate was filtered out, washed with ethyl acetate, then dried to obtain crude (±)-1-methyl-4-(2,4,6-trimethoxyphenyl)piperidin-3-one (26.5 g). The resulting solid (20 g) was suspended in 2-propanol (200 g). The mixture was warmed to 75° C. and stirred for 1 hour. The mixture was cooled to 20° C. and stirred for 30 minutes. The precipitate was filtered out, washed twice with 2-propanol (50 ml), and dried to obtain (±)-1-methyl-4-(2,4,6-trimethoxyphenyl)piperidin-3-one hydrochloride (17.9 g, yield: 70%).

$^1$H-NMR (400 MHz, $CDCl_3$) δ: 1.90-1.97 (m, 1H), 2.33 (s, 1H), 2.38 (s, 3H), 2.45-2.52 (m, 1H), 2.81 (d, J=16.0 Hz, 1H), 2.89 (d, J=11.6 Hz, 1H), 3.44 (d, J=15.6 Hz, 1H), 3.73 (s, 6H), 3.78 (s, 3H), 3.87 (dd, J=11.8 Hz, 7.4 Hz, 1H), 6.12 (s, 2H)

The manufacturing method of Reference Example 1 is a method that is similar to Patent Literature 2 or 3 or Non Patent Literature 2 and requires an ultralow temperature for reaction. Thus, the steps are complex and usable manufacturing facility would be limited, resulting in a significant problem for large-scale synthesis. Meanwhile, the manufacturing method of Example 1 does not require an ultralow temperature and can perform large-scale synthesis cost-effectively and readily at an ordinary manufacturing facility.

Reference Example 2: Manufacturing Method of (R)-1-methyl-4-(2,4,6-trimethoxyphenyl)piperidin-3-one dibenzoyl-D-tartrate

[Chemical Formula 36]

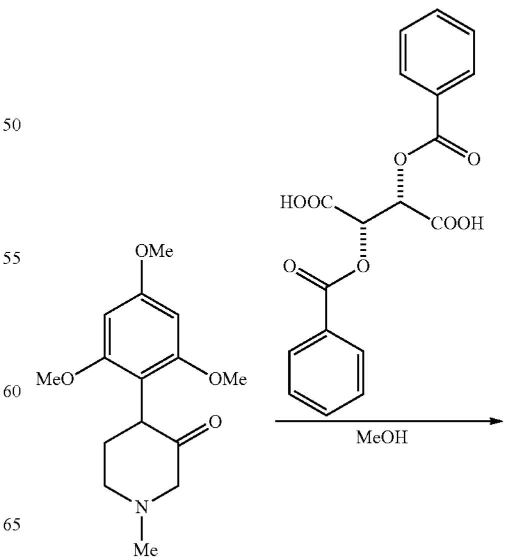

-continued

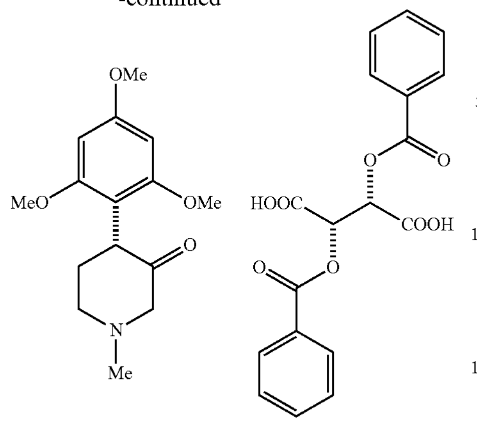

Under a nitrogen atmosphere, (±)-1-methyl-4-(2,4,6-trimethoxyphenyl)piperidin-3-one (15 g) and (+)-dibenzoyl-D-tartrate (21.2 g) were dissolved in methanol (68.2 g) at 65° C., and the mixture was stirred for 1 hour at 65° C. This was cooled over 6 hours to 0° C. and stirred overnight at 0° C. The precipitate was filtered out, washed twice with cold methanol (30 g), and dried to obtain a first crystal of (R)-1-methyl-4-(2,4,6-trimethoxyphenyl)piperidin-3-one (+)-dibenzoyl-D-tartrate (20.2 g, yield: 59%). The filtrate washing solution (133.5 g) was concentrated under reduced pressure to 33.3 g and warmed to 65° C. After cooling to 55° C., (R)-1-methyl-4-(2,4,6-trimethoxyphenyl)piperidin-3-one (+)-dibenzoyl-D-tartrate (7 mg) was added. The mixture was stirred for 1 hour and cooled over 6 hours to 0° C., and stirred overnight at 0° C. The precipitate was filtered out, washed twice with cold methanol (9.6 g), and dried to obtain a second crystal of (R)-1-methyl-4-(2,4,6-trimethoxyphenyl)piperidin-3-one (+)-dibenzoyl-D-tartrate 4.2 g, yield: 12%).

$^1$H-NMR (400 MHz, DMSO-d6) δ: 1.80-1.85 (m, 1H), 2.18-2.28 (m, 1H), 2.46 (s, 3H), 2.71-2.79 (m, 1H), 3.05-3.09 (m, 1H), 3.15-3.19 (m, 1H), 3.43-3.48 (m, 1H), 3.70 (s, 6H), 3.76 (s, 3H), 3.83 (dd, J=12.0 Hz, 6.8 Hz, 1H), 5.79, (s, 2H), 6.22 (s, 2H), 7.56 (dd, J=7.8 Hz, 7.8 Hz, 4H), 7.70 (dd, J=7.4 Hz, 7.4 Hz, 2H), 7.98 (d, J=7.6 Hz)

The manufacturing method of Reference Example 2 is a method that is similar to Patent Literature 1 or Non Patent Literature 1, which concentrates the filtrate of a first crystal and further obtains a second crystal. Thus, the method has steps that are complex and time intensive, and is unsuited for large-scale synthesis. The yield is also lower compared to Example 2. Meanwhile, the method of Example 2 is a method that can achieve a 79% yield from only a single crystallization and can be cost-effectively and readily applied in industrial use.

Reference Examples 3 to 7 confirmed hereinafter that alvocidib can be manufactured efficiently with cis-(−)-flocinopiperidol manufactured by using the invention of the present application.

Reference Example 3: Manufacturing Method of cis-(−)-acetoflocinopiperidol

[Chemical Formula 37]

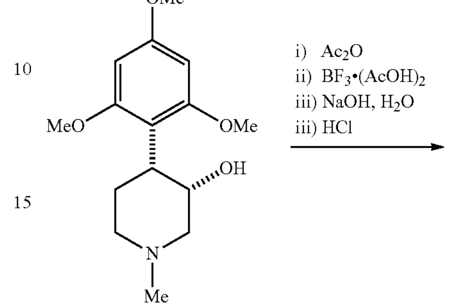

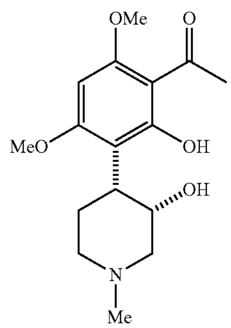

Under a nitrogen atmosphere, anhydrous acetic acid (80 g) was cooled to 6° C., and cis-(−)-flocinopiperidol (100 g) was added in 30 minutes while maintaining the internal temperature at 25° C. or lower. The mixture was incubated for 4 hours at 13 to 18° C. and cooled to 14° C. A boron trifluoride-acetic acid complex (200 g) was added dropwise over 30 minutes while maintaining the internal temperature at 45° C. or lower. The mixture was warmed to 55° C. and incubated for 5 hours. The mixture was cooled to 25° C. Water (184 g) was added dropwise at 35° C., and a dropping funnel was washed with water (90 g). The mixture was incubated for 3 hours at 35° C., and 30% sodium hydroxide water (900 g) was added dropwise at 40 to 55° C. The mixture was warmed to 60° C., then incubated for 1 hour, and cooled to 20° C. The solution was added to butanol (1111 g). Concentrated hydrochloric acid (138 g) was added dropwise at 30° C. or lower, and the pH was adjusted to 11.2 with concentrated hydrochloric acid (37.7 g). The aqueous layer was extracted with butanol (270 g). The organic layer was washed with water (300 g). After separation, the organic layer was washed with hydrochloric acid (mixture of 5.5 g of concentrated hydrochloric acid and 200 g of water), and the solution was separated. This was further washed with water (200 g) and separated. The organic layer was concentrated under reduced pressure to 222 g. Diisopropyl ether (220 g) was added to the residue, and the mixture was warmed to 65° C. The mixture was incubated for 1 hour at 65° C., then cooled to 0° C., and incubated for 1 hour. The precipitate was filtered out, washed twice with diisopropyl ether (73 g), and dried to obtain cis-(−)-acetoflocinopiperidol (123 g, yield: 92%).

$^1$H-NMR (400 MHz, DMSO-d6) δ: 1.22 (d, J=11.6 Hz, 1H), 1.90 (dd, J=11.0 Hz, 11.0 Hz, 1), 2.03 (d, J=9.6 Hz, 1H), 2.17 (s, 3H), 2.47 (s, 3H), 2.78-2.87 (m, 3H), 3.08-3.13 (m, 3H), 3.71 (s, 1H), 3.82 (s, 3H), 3.83 (s, 3H)

Reference Example 4: Manufacturing Method of cis-(−)-flavodimethoxol hydrochloride

[Chemical Formula 38]

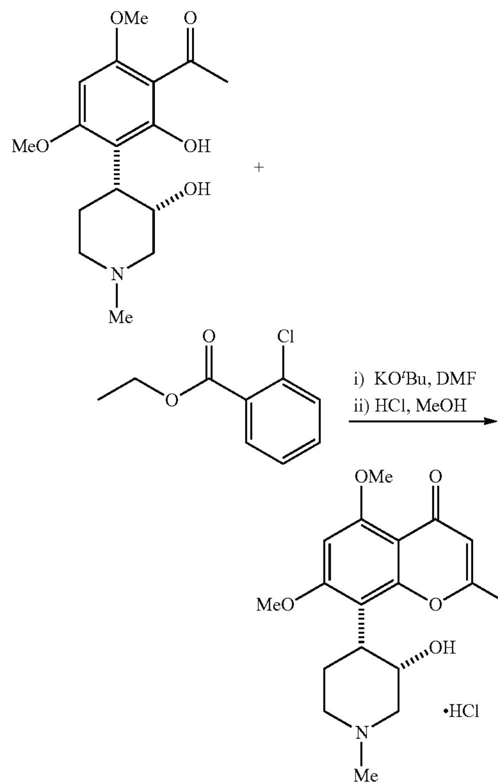

Under a nitrogen atmosphere, potassium tert-butoxide (80.3 g) was added to and dissolved in DMF (373 g). The mixture was cooled to 5° C., and cis-(−)-acetoflocinopiperidol (75 g) was added, while being maintained at 12° C. or lower. The mixture was incubated for 1 hour and 30 minutes at 25° C., and ethyl 2-chlorobenzoate (116 g) was added in 30 minutes while maintaining the internal temperature at 25° C. The mixture was warmed to 30° C. and incubated for 6 hours. The mixture was cooled to 16° C., and concentrated hydrochloric acid (458 g) was added dropwise at 50° C. or lower. The mixture was washed with water (19 g), and this was also added. The mixture was incubated and stirred for 6 hours and 30 minutes at 50° C., and cooled to 25° C. Water (773 g) was added, and 30% sodium hydroxide water (614 g) was added dropwise. The pH was adjusted to 11.1 with 30% sodium hydroxide water (69 g), and butanol (243 g) was added. The solution was separated. The aqueous layer was extracted with butanol (243 g), and the organic layer was combined. The mixture was concentrated under reduced pressure at 65° C. (distillation volume of 603 g) and cooled to 25° C. Methanol (269 g) was added to the residue. The mixture was incubated for 30 minutes and filtered. The residue was washed with methanol (30 g) and combined with the filtrate. Concentrated hydrochloric acid (32 g) was added dropwise to the filtrate washing solution. The mixture was incubated for 40 minutes at 25° C. cis-(−)-Flavodimethoxol hydrochloride (1.1 g) was added. The mixture was stirred for 30 minutes at 25° C. and then diisopropyl ether (544 g) was added dropwise over 45 minutes. The mixture was incubated for 1 hour at 20° C. The precipitate was filtered out and washed with a mixture of diisopropyl ether (163 g) and methanol (89 g). The precipitate was washed twice with diisopropyl ether (163 g) to obtain crude cis-(−)-flavodimethoxol hydrochloride (102.6 g, yield: 92%). Under a nitrogen atmosphere, crude cis-(−)-flavodimethoxol hydrochloride (90 g) was dissolved in a mixture of 2-propanol (113 g) and water (216 g) at 40° C. The mixture thereof was incubated for 30 minutes. The mixture was cooled to 30° C., and cis-(−)-flavodimethoxol hydrochloride (0.9 g) was added. The mixture was incubated for 1 hour. The mixture was cooled to 5° C. over 3 hours and incubated for 2 hours at 5° C. The precipitate was washed with 2-propanol (70 g) and dried to obtain cis-(−)-flavodimethoxol hydrochloride (76.2 g, yield: 87%).

$^1$H-NMR (400 MHz, DMSO-d6) δ: 1.83 (d, J=13.2 Hz, 1H), 2.71 (s, 3H), 3.09-3.21 (m, 4H), 3.29-3.33 (m, 1H), 3.44 (d, J=11.2 Hz, 1H), 3.92 (d, J=3.2 Hz, 3H), 3.95 (d, J=2.8 Hz, 3H), 3.99 (s, 1H), 5.46-5.48 (m, 1H), 6.34 (d, J=2.8 Hz, 1H), 6.71 (d, J=3.2 Hz, 1H), 7.54-7.62 (m, 2H), 7.67-7.69 (m, 1H), 7.80-7.82 (m, 1H), 9.49 (s, 1H)

Reference Example 5: Manufacturing Method of Crude Alvocidib Free Form

[Chemical Formula 39]

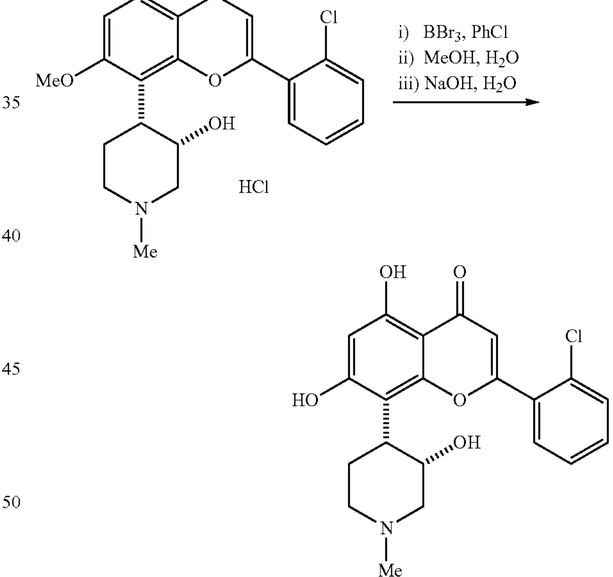

Under a nitrogen atmosphere, cis-(−)-flavodimethoxol hydrochloride (40 g) was dissolved in chlorobenzene (354 g) and the mixture was warmed to 75° C. Boron tribromide (177 g) was added dropwise over 4 hours while maintaining the internal temperature at 75° C. A dropping funnel was washed with chlorobenzene (4 g) and added. The mixture was warmed to 80° C. and incubated for 6 hours. The mixture was cooled to room temperature and stirred overnight. The mixture was warmed to 100° C., and incubated and stirred for 2 hours and 30 minutes. The mixture was cooled to 20° C., and a mixture of water (40 g) and methanol (63 g) was added dropwise over 3 hours while maintaining the internal temperature at 25° C. The mixture was incubated and stirred for 15 minutes at 25° C., and then methanol (63 g) was added dropwise while maintaining the internal temperature at 25° C. The mixture was stirred overnight at 25° C. The mixture was warmed to an internal temperature of 72 to 79° C. and concentrated by atmospheric distillation (distillation volume of 79 g). The mixture was concentrated by atmospheric distillation while adding a mixture of water (18 g), methanol (527 g), and chlorobenzene (239 g) dropwise (distillation volume of 799 g). The mixture thereof was cooled to 50° C., and 26.5% sodium hydroxide water (25 g) was added dropwise. The mixture was warmed to an internal temperature of 72 to 79° C. and continuously concentrated by atmospheric distillation while adding a mixture of water (6 g), methanol (176 g), and chlorobenzene (80 g) dropwise (distillation volume of 263 g). After cooling the mixture thereof to 40° C., the mixture was warmed again to 72° C. and concentrated under atmospheric pressure. The mixture was cooled to 50° C. Methanol (112 g) and chlorobenzene (127 g) were added, and an aqueous 26.5% sodium hydroxide solution (14 g) was added dropwise. The mixture was incubated for 1 hour at 50° C. After adding water (160 g) dropwise, the mixture was cooled to 20° C. The mixture was incubated for 1 hour at 20° C. The precipitate was filtered out and washed with a mixture of water (140 g) and methanol (48 g). The precipitate was suspended in water (140 g) and methanol (48 g). The washing solution was added and the mixture was incubated. A crystal was filtered out, washed with a mixture of water (140 g) and methanol (48 g), washed four times with water (200 g), and then dried to obtain a crude alvocidib free form (29.7 g, yield; 86.1%).

$^1$H-NMR (400 MHz, MeOH-d4) δ: 1.59 (d, J=11.6 Hz, 1H), 2.75 (s, 3H), 2.97 (ddd, J=12.4 Hz, 12.4 Hz, 2.9 Hz, 1H), 3.04-3.14 (m, 2H), 3.30-3.32 (m, 1H), 3.41 (d, J=12.0 Hz, 1H), 3.57-3.61 (m, 1H), 4.17 (s, 1H), 6.03 (s, 1H), 6.30 (s, 1H), 7.49 (ddd, J=7.4 Hz, 7.4 Hz, 1.6 Hz, 1H), 7.54 (ddd, J=7.6 Hz, 7.6 Hz, 1.7 Hz, 1H), 7.60 (dd, J=8.4 Hz, 1.2 Hz, 1H), 7.68 (dd, J=7.4 Hz, 1.8 Hz, 1H)

Reference Example 6: Manufacturing Method of Alvocidib Hydrochloride Ethanolate

[Chemical Formula 40]

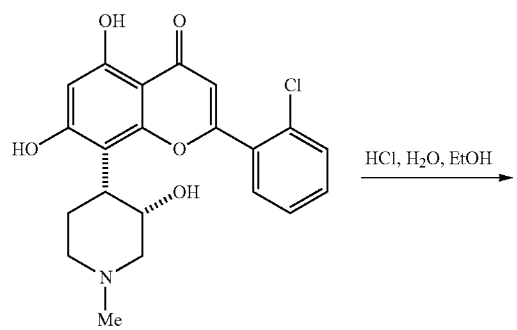

-continued

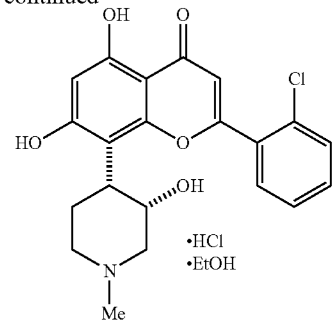

Under a nitrogen atmosphere, a crude alvocidib free form (20 g) was dissolved in ethanol (228 g). The mixture was warmed to 35° C. Concentrated hydrochloric acid (10.4 g) was added dropwise while maintaining an internal temperature of 35° C., and a dropping funnel was washed with ethanol (4.6 g). The mixture was warmed to 74° C. and hot-filtered. The filtration paper was washed with ethanol (23 g). The filtrate and washing solution were combined and concentrated under atmospheric pressure (distillation volume of 190 g). The mixture was cooled to 25° C. and incubated overnight. The mixture was cooled to −10° C. and incubated for 2 hours. The precipitate was filtered out, washed with cold ethanol (94 g), and dried to obtain alvocidib hydrochloride ethanolate (22.4 g, yield: 93%).

$^1$H-NMR (400 MHz, MeOH-d4) δ: 1.17 (t, J=7.2 Hz, 3H), 1.83-1.91 (m, 1H), 2.86 (s, 3H), 3.09-3.21 (m, 2H), 3.32-3.35 (m, 1H), 3.45 (ddd, J=12.6 Hz, 2.4 Hz, 2.4 Hz, 1H), 3.50-3.53 (m, 1H), 3.60 (q, J=7.1 Hz, 2H), 3.69-3.74 (m, 1H), 4.26 (s, 1H), 6.34 (s, 1H), 6.48 (s, 1H), 7.52 (ddd, J=7.3 Hz, 7.3 Hz, 1.3 Hz, 1H), 7.58 (ddd, J=7.6 Hz, 7.6 Hz, 1.9 Hz, 1H), 7.62 (dd, J=7.8 Hz, 1.4 Hz, 1H), 7.76 (dd, J=7.6 Hz, 1.6 Hz, 1H)

Reference Example 7: Manufacturing Method of Alvocidib Hydrochloride

[Chemical Formula 41]

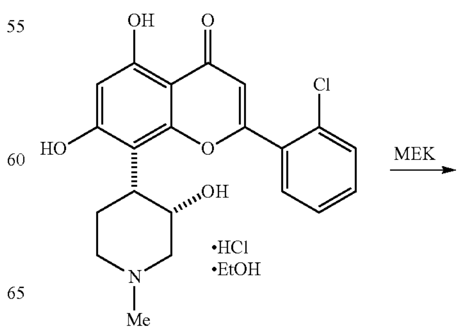

-continued

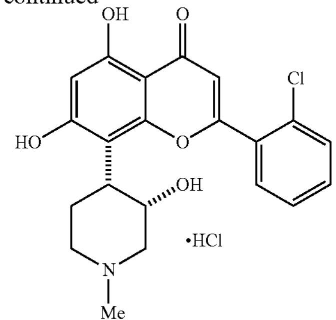

Under a nitrogen atmosphere, alvocidib hydrochloride ethanolate (20 g) was dissolved in methyl ethyl ketone (297 g). The mixture was warmed to 80° C. and incubated for 4 hours. The mixture was cooled to 22° C. and incubated for 1 hour. The precipitate was filtered out, washed with methyl ethyl ketone (69 g), and dried to obtain alvocidib hydrochloride (17.7 g, yield: 98%, HPLC purity: 99.6 area %, optical purity: >99.9% ee).

$^{1}$H-NMR (400 MHz, MeOH-d4) δ: 1.83-1.91 (m, 1H), 2.85 (s, 3H), 3.10-3.22 (m, 2H), 3.34 (s, 1H), 3.42-3.46 (m, 1H), 3.49-3.53 (m, 1H), 3.69-3.73 (m, 1H), 4.26 (s, 1H), 6.34 (s, 1H), 6.48 (s, 1H), 7.52 (ddd, J=7.4 Hz, 7.4 Hz, 1.5 Hz, 1H), 7.58 (ddd, J=7.8 Hz, 7.8 Hz, 2.0 Hz, 1H), 7.63 (dd, J=7.8 Hz, 1.4 Hz, 1H), 7.75 (dd, J=7.4 Hz, 1.4 Hz, 1H)

As described above, the present invention is exemplified by the use of its preferred embodiments. However, it is understood that the scope of the present invention should be interpreted based solely on the Claims. The present application claims priority to Japanese Patent Application No. 2019-79299 (filed on Apr. 18, 2019) with the Japan Patent Office. The entire content thereof is incorporated herein by reference. It is also understood that any patent, any patent application, and any references cited herein should be incorporated herein by reference in the same manner as the contents are specifically described herein.

INDUSTRIAL APPLICABILITY cis-(−)-Flocinopiperidol, which is an intermediate of alvocidib that is useful as a pharmaceutical product, can be manufactured safely and cost-effectively at a high yield, with high selectivity, and at a high purity by using the manufacturing method of the invention.

The invention claimed is:

1. A manufacturing method of cis-(−)-flocinopiperidol represented by formula (I):

(I)

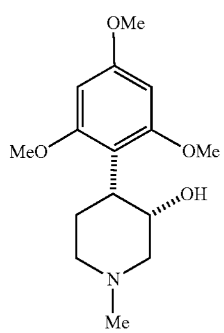

or a salt thereof or a solvate thereof, comprising the following steps:

(b) forming (R)-1-methyl-4-(2,4,6-trimethoxyphenyl)-3-piperidinone (+)-dibenzoyl-D-tartrate represented by formula (5):

(5)

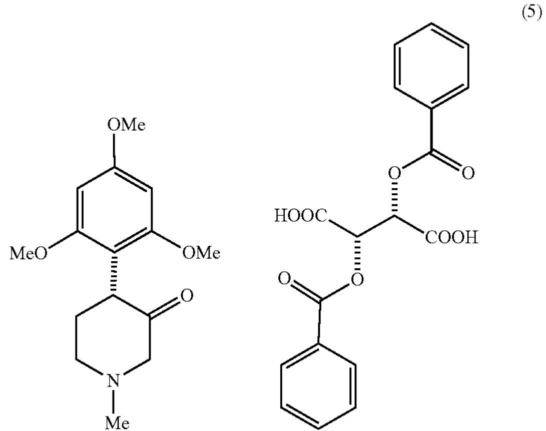 [SMILES: COc1cc(OC)c([C@H]2CCN(C)CC2=O)c(OC)c1 ; O=C(O[C@H](C(=O)O)[C@H](OC(=O)c1ccccc1)C(=O)O)c1ccccc1]

or a solvate thereof by:

(i) reacting (+)-1-methyl-4-(2,4,6-trimethoxyphenyl)-3-piperidinone represented by formula (3):

(3)

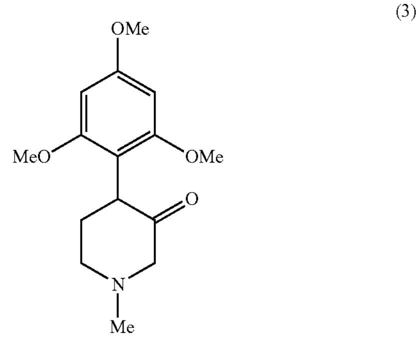

or a salt thereof or a solvate thereof with (+)-dibenzoyl-D-tartrate represented by formula (4):

(4)

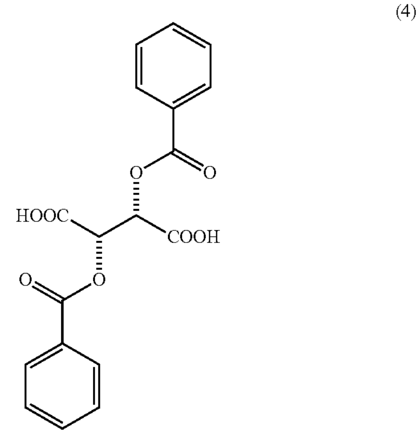

or a salt thereof or a solvate thereof in a reaction solvent;

(ii) precipitating (R)-1-methyl-4-(2,4,6-trimethoxyphenyl)-3-piperidinone (+)-dibenzoyl-D-tartrate represented by formula (5) by adding a poor solvent to a reaction solution of step (i), wherein the poor solvent is an ether-based solvent selected from diisopropyl ether, 1,2-dimethoxyethane, tetrahydrofuran, 2-methyltetrahydrofuran and cyclopentyl methyl ether;

(c) reacting (R)-1-methyl-4-(2,4,6-trimethoxyphenyl)-3-piperidinone (+)-dibenzoyl-D-tartrate represented by formula (5):

(5)

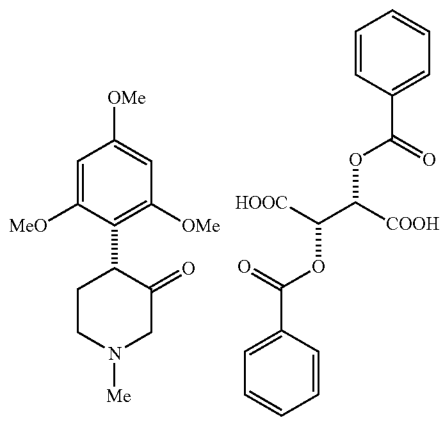

or a solvate thereof with an organic base in a solvent to manufacture (R)-1-methyl-4-(2,4,6-trimethoxyphenyl)-3-piperidinone represented by formula (6):

(6)

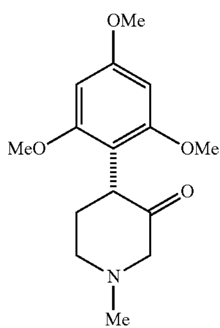

or a salt thereof or a solvate thereof, wherein the organic base is a tertiary amine; and (d) reacting (R)-1-methyl-4-(2,4,6-trimethoxyphenyl)-3-piperidinone represented by formula (6):

(6)

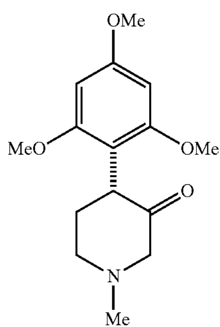

or a salt thereof or a solvate thereof with a compound of formula (7):

(7)

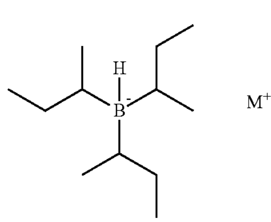

or a solvate thereof, in a solvent, to manufacture cis-(−)-flocinopiperidol represented by formula (I):

(I)

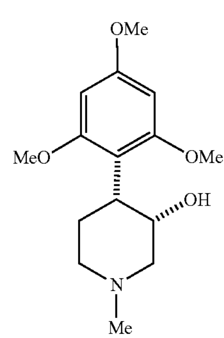

or a salt thereof or a solvate thereof, wherein M in formula (7) is lithium, sodium, or potassium.

2. The manufacturing method of claim 1, wherein M in formula (7) used in step (d) is lithium.

3. The manufacturing method of claim 1, wherein a compound of formula (I) or a solvate thereof is obtained in step (d) by extracting a product after a reduction reaction with an acidic aqueous solution and increasing the pH of the extraction solution.

4. The manufacturing method of claim 1, wherein a compound of formula (I) or a solvate thereof is obtained in step (d) by extracting a product after a reduction reaction with an acidic aqueous solution and dripping the extraction solution into a basic aqueous solution.

5. The manufacturing method of claim 3, wherein the pH of the acidic aqueous solution is 6.0 to 6.5 in step (d).

6. The manufacturing method of claim 3, wherein the pH of the acidic aqueous solution is 6.0 in step (d).

7. The manufacturing method of claim 1, wherein the solvent used in step (c) is an ether-based solvent.

8. The manufacturing method of claim 1, wherein step (d) is performed using a base-neutralized product in a state of a solution without isolation in step (c).

9. The manufacturing method of claim 1, wherein the reaction solvent in step (b) is at least one reaction solvent selected from an ester-based solvent, an ether-based solvent, an alcohol-based solvent, an amide-based solvent, a nitrile-based solvent, and an aromatic solvent.

10. The manufacturing method of claim 1, wherein the reaction solvent used in step (b) is an alcohol-based solvent.

11. The manufacturing method of claim 1, further comprising the following step (a) before step (b):

(a) reacting (+)-1-methyl-4-(2,4,6-trimethoxyphenyl) piperidine-3-ol represented by formula (1):

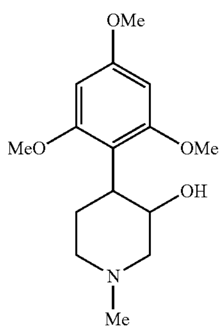

or a salt thereof or a solvate thereof with a compound represented by formula (2):

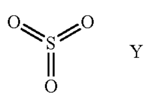

or a salt thereof or a solvate thereof and dialkyl sulfoxide to manufacture (+)-1-methyl-4-(2,4,6-trimethoxyphenyl)-3-piperidinone represented by formula (3):

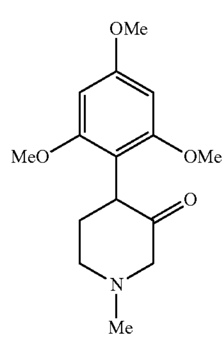

or a salt thereof or a solvate thereof.

12. The manufacturing method of claim 11, wherein Y in formula (2) used in step (a) is pyridine.

13. The manufacturing method of claim 11, wherein the reaction in step (a) is performed at a temperature of −10° C. or higher.

14. The manufacturing method of claim 11, wherein the reaction in step (a) is performed at a temperature from 0° C. to 30° C.

* * * * *